US006632418B2

(12) United States Patent
Altenbach et al.

(10) Patent No.: US 6,632,418 B2
(45) Date of Patent: Oct. 14, 2003

(54) RADIOLIGANDS AND THEIR USE FOR IDENTIFYING POTASSIUM CHANNEL MODULATORS

(75) Inventors: Robert J. Altenbach, Chicago, IL (US); Gary A. Rotert, Vernon Hills, IL (US); William A. Carroll, Evanston, IL (US); Murali Gopalakrishnan, Libertyville, IL (US); Eduardo Jose Vicente Molinari, Chicago, IL (US); Rachel A. Davis-Taber, Grayslake, IL (US); Victoria Eleanor Sarah Scott, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 24 days.

(21) Appl. No.: 10/208,237

(22) Filed: Jul. 30, 2002

(65) Prior Publication Data

US 2003/0065182 A1 Apr. 3, 2003

Related U.S. Application Data

(60) Provisional application No. 60/308,703, filed on Jul. 30, 2001.

(51) Int. Cl.[7] .................. A61K 51/00; C07D 491/153; C07D 491/04; A61M 36/04

(52) U.S. Cl. .................. 424/1.85; 546/92; 546/90; 546/89; 546/80

(58) Field of Search .................. 424/1.85; 546/92, 546/90, 89, 80

(56) References Cited

U.S. PATENT DOCUMENTS

5,328,830 A 7/1994 Janis et al.
6,191,140 B1 * 2/2001 Carroll et al. .............. 514/297

FOREIGN PATENT DOCUMENTS

WO 00/24743 5/2000

OTHER PUBLICATIONS

Acheson, *J. Chem. Soc.*, pp. 650–660 (1961).
Allevi, *Tetrahedron Assymmetry*, 8:93–100 (1997).
Arnett, Edward M., *J. Amer. Chem. Soc.* 109:809–812 (1987).
Avison, *Nature (London)*, 154:459 (1944).
Badder, *J. Indian Chem. Soc.*, 53:1053 (1976).
Bergel, *Nature*, (London) 155:481 (1945).
Berry, Nicola M., *Synthesis*, 6:476–480 (1986).
Binder, *Arch. Pharm. (Weinheim Ger.)*, 314:557–564 (1981).
Bray, K.M., et al., *J. Biol. Chem.*, 267:11689–11692 (1992).
Burgess, *J. Amer. Chem. Soc.*, 112:7434–7435 (1990).
Burgess, *J. Amer. Chem. Soc.*, 113:6129–6139 (1991).
Challenger, *J. Chem. Soc.*, 61:68 (1959).
Champagne, *Can. J. Chem.*, 42:212–222 (1964).
Cheng and Prusoff, *Biochem. Pharmacol.*, 22:3099–3108 (1973).
Craig, *J. Org. Chem.*, 32:3743–3749 (1967).
Crossley, *J. Chem. Soc.*, 107:605 (1915).
d'Angelo, *Tett. Lett.*, 32:3063–3066 (1991).
Demir, *J. Prakt. Chem./Chem.–Ztg.*, 339:553–563 (1997).
Demir, *Tetrahedron Lett.*, 30:1705–1708 (1989).
Deno, *J. Amer. Chem. Soc.*, 90:4085–4088 (1968).
Deshmukh, *Synth. Commun.*, 26:1657–1662 (1996).
Dowd, *Tetrahedron*, 47:4847–4860 (1991).
Duus, *Tetrahedron*, 37:2633–2640 (1981).
Edafiogho, *J. Med. Chem.*, pp. 2798–2805 (1992).
Er, *Helv. Chim. Acta.*, 75:2265–2269 (1992).
Fadda, *J. Indian Chem. Soc.*, 67:915–917 (1990).
Fehnel, *J. Amer. Chem. Soc.*, 77:4241–4242 (1955).
Fiesselmann, *Chem. Ber.*, 87:848, 854 (1954).
Fredga, *Ark. Kemi*, 16B(8):5 (1943).
Ghosh, *J. Med. Chem.*, 37:1177–1188 (1994).
Gilling, *J. Chem. Soc.*, 103:2033 (1913).
Gopalakrishnan, M., et al., *Am. J. Physiol.*, 261:H1979–H1987 (1991).
Gopalakrishnan, M., et al., *Journal of Pharmacology and Experimental Therapeutics*, 257:1162–1171 (1991).
Hamer, *Tetrahedron Lett.*, 27:2167–2168 (1986).
Hinkel, *J. Chem. Soc.*, p. 814 (1931).
Hodgson, *J. Chem. Soc.*, p. 2425 (*1927*).
Hofer, Roger, *Helv. Chim. Acta*, 68:969–974 (1985).
Hoffman, F. J., Jr., et al., *Biochem. Biophys. Res. Commun.*, 190:551–558 (1993).
Janis, R.A., et al., *Eur. J. Pharmacol.*, 82:191–194 (1982).
Kato, *Chem. Pharm. Bull.* 34:486–495 (1986).
Kikani, B., *Synthesis*, 2:176 (1991).
Knoevenagel, *Chem. Ber.*, 35:2182 (1902).
Komasov, *Bull. Acad. Sci. USSR Div. Chem. Sci.* (Engl. Trans.), pp. 81–85 (1963).
Kvita, *Collect. Czech. Chem. Commun.*, 22:1064 (1957).
Landesberg, *J. Org. Chem.*, 33:3374–3382 (1968).
Larsson, *Chem. Ber.*, 67:759 (1934).
Larsson, *Sven. Kem. Tidskr.* 57:248 (1945).
Loffler-Walz, C., et al., *Br. J. Pharmacol*, 123 :1395–1402 (1998).
Lowry, O.H., et al., *J. Biol. Chem.*, 193:265–275 (1951).
Martani, *Ric. Sci.*, 29:520, 523 (1959).
Matoba, *Chem. Pharm. Bull.*, pp. 2955–2956 (1983).
Midland, M., *Tetrahedron*, 40:1371–1380 (1984).
Morgan, *J. Amer. Chem. Soc.*, 79:422 (1957).
Mukherjee, *Indian J. Chem. Sect. B*, 23:193–198 (1984).
Nakagawa, *Heterocycles*, 13:477–495 (1979).
Nilsson, *Acta Chem. Scand. Ser. B*, 35:667–668 (1981).

(List continued on next page.)

Primary Examiner—Charanjit S. Aulakh
(74) Attorney, Agent, or Firm—Michaerl J. Ward

(57) ABSTRACT

The present invention relates to novel radioligands and test methods using those radioligands in screening compounds.

17 Claims, 1 Drawing Sheet

OTHER PUBLICATIONS

Figure 1:
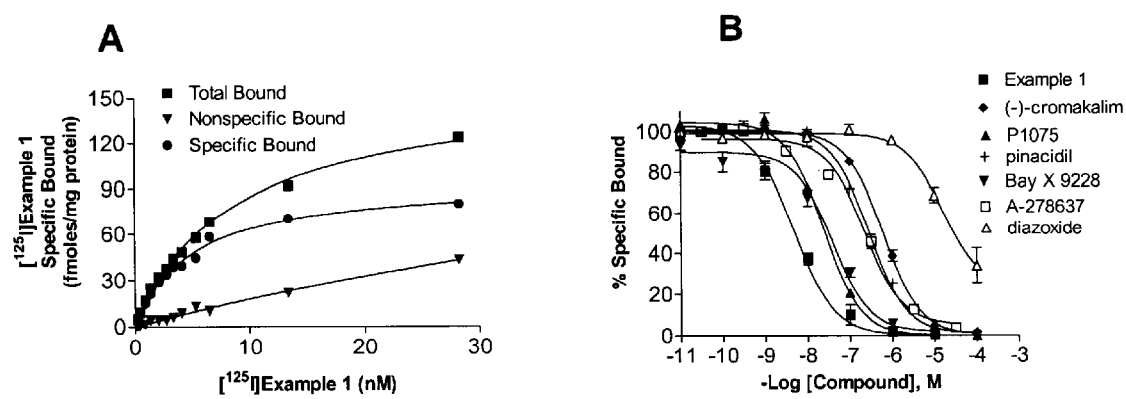

Pearson, *Org. Synth. Coll.,* Vol V:117 (1973).
Ranu, *Tetrahedron,* 48:1327–1332 (1992).
Reinhoudt, *Synthesis,* pp 368–370 (1978).
Rothstein, *J. Chem. Soc.* p. 2017 (1926).
Russ, U., et al., *Br. J. Pharmacol.,* 122:1119–1126 (1997).
Sato, Masayuki, *Tetrahedron,* 5:1665–1668 (1994).
Sato, Masayuki, *Tetrahedron Lett.,* 31:7463–7466 (1990).
Schinzer, *Liebigs Ann. Chem.,* 2:139–144 (1992).
Schoeberl, Justus, *Liebigs Ann. Chem.,* 599:140, 151 (1956).
Smith, R., *J. Med. Chem.,* 31:1558–1566 (1988).
Stetter, *Chem. Ber.,* 91:374 (1958).
Tabuchi, Hiroyasu, *J. Chem. Soc. Perkin,* (*Trans. 1*) pp. 125–134 (1994).
Tabuchi, Hiroyasu, *J. Org. Chem.* 59:4749–4759 (1994).
Takano, *Synthesis,* 12:1253–1256 (1993).
Terasawa, *J. Org. Chem.,* 42:1163–1169 (1977).
Woodward, *J. Amer. Chem. Soc.,* 68:2229–2234 (1946).
Yamamoto, Y., *J. Amer. Chem. Soc.,* 114:121–125 (1992).
Zenyuk, A. A., *Chem. Nat. Compd.* (*Engl. Transl.*) 27:400–403 (1991).
Zenyuk, A. A., *J. Org. Chem. USSR* (*Engl. Transl.*) 26:1926–1927 (1990).

\* cited by examiner

RADIOLIGANDS AND THEIR USE FOR IDENTIFYING POTASSIUM CHANNEL MODULATORS

This application claims priority from U.S. Provisional Application Serial No. 60/308,703, filed Jul. 30, 2001, incorporated herein by reference.

TECHNICAL FIELD

The present invention relates to novel radioligands and to methods for detecting specific activity of compounds. More particularly, the present specification discloses assays for detecting the binding of compounds to sites that regulate potassium channels.

BACKGROUND OF THE INVENTION

Potassium channels play important roles in regulating cell membrane excitability. In particular, ATP-sensitive potassium channels that are inhibited by intracellular ATP link cellular metabolism with membrane excitability in various cell types including cardiac, smooth muscle, neurons and secretory cells. In these cell types, $K_{ATP}$ channels modulate physiological processes including insulin secretion from pancreas, leptin release from hypothalamic neurons, synaptic transmission and excitability of cardiac, vascular and nonvascular smooth muscles. Openers of various $K_{ATP}$ channels can alter the cell's resting membrane potential and in turn cellular excitability to regulate these diverse processes. A number of diseases or conditions can be treated with therapeutic agents that open potassium channels. Such diseases or conditions include asthma, epilepsy, hypertension, sexual dysfunction, pain, migraine, urinary incontinence, stroke and neurodegeneration.

[$^3$H]P1075 is a known radioligand for the ATP-sensitive potassium channel described by Brya et al., 1992. [$^3$H]Bay X 9228 is another known radioligand for the ATP-senstive potassium channel. U.S. Pat. No. 5,328,830 discloses the utilization of tritiated (+)-N-(2-ethoxyphenyl)-N'-(1,2,2-trimethyl propyl)-2-nitroethene-1,1-diamine ([$^3$H]CMPD), for assaying compounds whose activity is specific for ATP-sensitive potassium channels. However, the utility of these ligands are limited. These assays generally require intact cell or tissue preparations with large inherent variability due to poor specific activity and poor binding affinities Loffler-Walz, C., Quast, U. (1998) Br. J. Pharmacol., 123, 1395–1402.

Accordingly, a novel radioligand with improved potency and higher specific activity would be useful for characterization of $K_{ATP}$ channels in various tissues in addition to further investigation of the mechanism of action of novel potassium channel modulators with native and recombinant $K_{ATP}$ complex. The present invention relates to novel 1,4-dihydropyridine radioligands that have higher affinities and higher specific activity in interacting with the ATP-sensitive potassium channel. Specifically, the present invention discloses assays using novel 1,4-dihydropyridine radioligands for screening and identification of compounds that interact with ATP-sensitive potassium channels.

SUMMARY OF THE INVENTION

In one embodiment, the present invention discloses compounds of formula I:

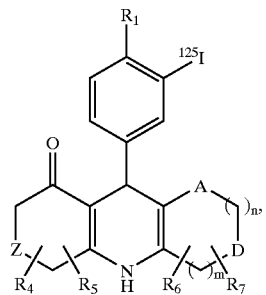

or salts thereof wherein
n is an integer of 0–1;
m is an integer of 1–2;
provided that when n is 1, then m is 1;
A is selected from C(O) and S(O)$_2$;
D is selected from O, S and CR$_2$R$_3$;
Z is selected from O and S;
R$_1$ is selected from alkyl, cyano, haloalkoxy, haloalkyl, halogen and nitro; and
R$_2$, R$_3$, R$_4$, R$_5$, R$_6$ and R$_7$ are each independently selected from hydrogen and alkyl;
provided that when A is S(O)$_2$; then D is CR$_2$R$_3$; and
further provided that when D is S; then n is 1 and A is C(O).

The compounds of the present invention are novel radioligands that bind to the ATP sensitive potassium channels. The present invention also relates to a binding assay that can be used to evaluate compounds that bind to a site that regulates the function of the K$^+$ channel complex. These compounds are useful for high throughput screening of compound libraries to identify novel ligands interacting with the ATP-sensitive potassium channels. Such radioligands could also be of utility in: (i) characterization of recombinant ATP-sensitive channel subunits; (ii) use as a tool to identify novel $K_{ATP}$ channel subunits (iii) study distribution of $K_{ATP}$ channels in situ in various tissues in physiological and disease states and (iv) in vivo imaging of ATP-sensitive potassium channels, including photoemission computed tomography.

DETAILED DESCRIPTION OF THE INVENTION

In one embodiment, the present invention discloses compounds of formula I:

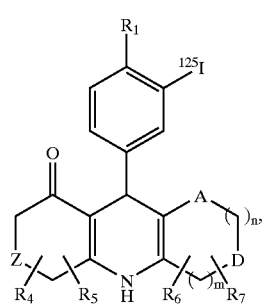

or salts thereof wherein
n is an integer of 0–1;
m is an integer of 1–2;

provided that when n is 1, then m is 1;
A is selected from C(O) and S(O)$_2$;
D is selected from O, S and CR$_2$R$_3$;
Z is selected from O and S;
R$_1$ is selected from alkyl, cyano, haloalkoxy, haloalkyl, halogen and nitro; and
R$_2$, R$_3$, R$_4$, R$_5$, R$_6$ and R$_7$ are each independently selected from hydrogen and alkyl;
provided that when A is S(O)$_2$; then D is CR$_2$R$_3$; and further provided that when D is S; then n is 1 and A is C(O).

In another embodiment, compounds of the present invention have formula (I) wherein R$_1$ is selected from alkyl, haloalkyl and halogen; R$_4$, R$_5$, R$_6$ and R$_7$ are each hydrogen; and m, n, A, D and Z are as defined in formula (I).

In another embodiment, compounds of the present invention have formula (I) wherein n is 0; A is S(O)$_2$; D is CR$_2$R$_3$; and m, Z, R$_1$, R$_2$, R$_3$, R$_4$, R$_5$, R$_6$ and R$_7$ are as defined in formula (I).

In another embodiment, compounds of the present invention have formula (I) wherein m is 1; n is 0; A is S(O)$_2$; D is CR$_2$R$_3$; Z is O; R$_2$, R$_3$, R$_4$, R$_5$, R$_6$ and R$_7$ are each hydrogen; and R$_1$ is as defined in formula (I).

In another embodiment, compounds of the present invention have formula (I) wherein n is 0; A is C(O); D is CR$_2$R$_3$; and m, Z, R$_1$, R$_2$, R$_3$, R$_4$, R$_5$, R$_6$ and R$_7$ are as defined in formula (I).

In another embodiment, compounds of the present invention have formula (I) wherein n is 0; A is C(O); D is O; and m, Z, R$_1$, R$_2$, R$_3$, R$_4$, R$_5$, R$_6$ and R$_7$ are as defined in formula (I).

In another embodiment, compounds of the present invention have formula (I) wherein m is 1; n is 0; A is C(O); D is O; Z is O; R$_4$, R$_5$, R$_6$ and R$_7$ are each hydrogen; and R$_1$ is as defined in formula (I).

In another embodiment, compounds of the present invention have formula (I) wherein n is 0; A is C(O); D is O; R$_4$, R$_5$ and R$_6$ are each hydrogen; R$_7$ is alkyl; m, Z and R$_1$ are as defined in formula (I).

In another embodiment, compounds of the present invention have formula (I) wherein m is 1; n is 0; A is C(O); D is O; Z is O; R$_4$, R$_5$ and R$_6$ are each hydrogen; R$_7$ is alkyl; and R$_1$ is as defined in formula (I).

In another embodiment, compounds of the present invention have formula (I) wherein m is 1; n is 1; A is C(O); D is O; and Z, R$_1$, R$_4$, R$_5$, R$_6$ and R$_7$ are as defined in formula (I).

In another embodiment, compounds of the present invention have formula (I) wherein m is 1; n is 1; A is C(O); D is O; R$_4$, R$_5$, R$_6$ and R$_7$ are each hydrogen; and Z and R$_1$ are as defined in formula (I).

In another embodiment, compounds of the present invention have formula (I) wherein m is 1; n is 1; A is C(O); D is O; Z is O; R$_4$, R$_5$, R$_6$ and R$_7$ are each hydrogen; and R$_1$ is as defined in formula (I).

As used throughout this specification and the appended claims, the following terms have the following meanings:

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "cyano," as used herein, refers to a —CN group.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The termer "nitrogen protecting group," or "N-protecting group," as used herein, refers to those groups intended to protect an amino group against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Commonly used N-protecting groups are disclosed in T. W. Greene and P. G. M. Wuts, Protective Groups in Organic Synthesis, 3rd edition, John Wiley & Sons, New York (1999).

The term "nitro," as used herein, refers to a —NO$_2$ group.

The radioligands of the present invention can be used in the form of salts derived from inorganic or organic acids. The salts can be prepared in situ during the final isolation and purification of the radioligands of the present invention or separately by reacting a free base function with a suitable organic acid. Examples of acids which can be employed to form salts include such inorganic acids as hydrochloric acid, hydrobromic acid, sulphuric acid and phosphoric acid and such organic acids as oxalic acid, maleic acid, succinic acid and citric acid.

The compounds and processes of the present invention will be better understood by reference to the following Schemes and Examples, which are intended as an illustration of, and not a limitation upon the scope of the invention. Furthermore, all citations contained within this document are hereby fully incorporated by reference. In particular, U.S. Pat. No. 6,191,140 is fully incorporated by reference.

The compounds of this invention can be prepared by a variety of synthetic routes. Representative procedures are shown in Schemes 1–24.

Scheme 1

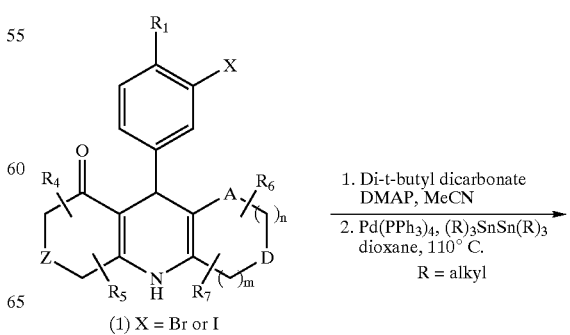

1. Di-t-butyl dicarbonate DMAP, MeCN
2. Pd(PPh$_3$)$_4$, (R)$_3$SnSn(R)$_3$ dioxane, 110° C.
R = alkyl (1) X = Br or I

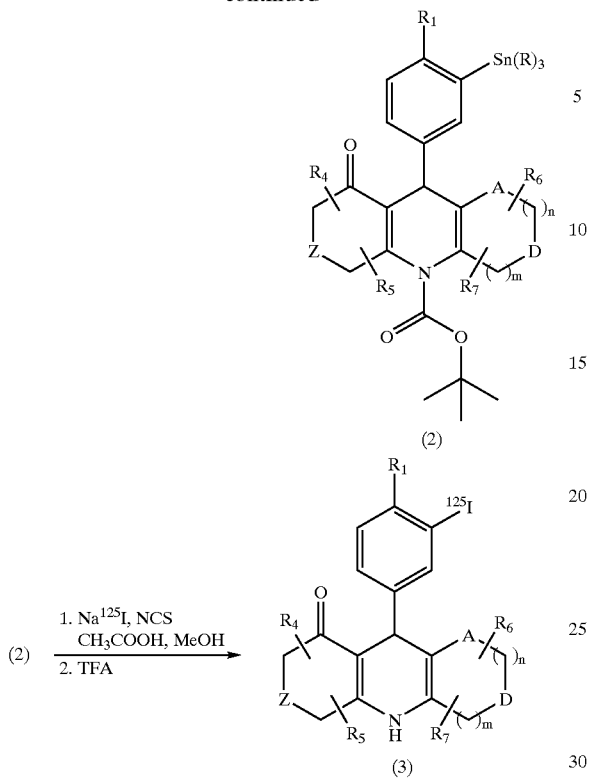

(2)

1. Na$^{125}$I, NCS
   CH$_3$COOH, MeOH
2. TFA (2) →

(3)

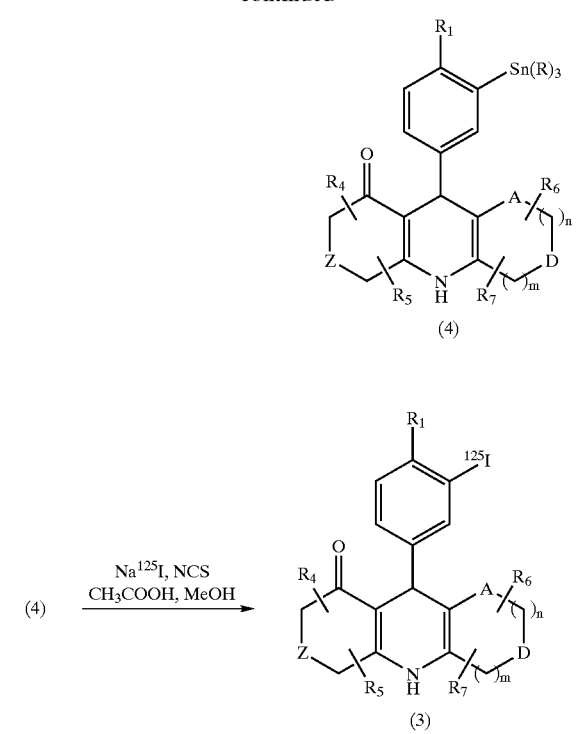

(4)

Na$^{125}$I, NCS
CH$_3$COOH, MeOH (3)

[$^{125}$I]Dihydropyridines of general formula (3), wherein A, D, Z, R$_1$, R$_4$, R$_5$, R$_6$, R$_7$, m and n are as defined in formula (I), can be prepared as described in Scheme 1. Compounds of general formula (1), wherein X is selected from Br or I, can be treated with a nitrogen protecting reagent such as di-tert-butyl dicarbonate in a solvent such as acetonitrile (MeCN) in the presence of 4-dimethylaminopyridine (DMAP) to provide N-protected dihydropyridines which can then be treated with a suitable tin reagent such as hexamethylditin in the presence of a palladium catalyst with heating in a solvent such as 1,4-dioxane to provide dihydropyridines of general formula (2). Dihydropyridines of general formula (2) can be treated with N-chlorosuccinimide (NCS) and an appropriate source of $^{125}$I such as Na$^{125}$I in a mixture of acetic acid and methanol to provide N-protected [$^{125}$I]dihydropyridines which can then be deprotected, for example with trifluoroacetic acid (TFA), to provide [$^{125}$I] dihydropyridines of general formula (3).

An alternative method of preparing [$^{125}$I] dihydropyridines of general formula (3), wherein A, D, Z, R$_1$, R$_4$, R$_5$, R$_6$, R$_7$, m and n are as defined in formula (I), can be used as described in Scheme 2. Compounds of general formula (1), wherein X is selected from Br or I, can be treated with a suitable tin reagent such as hexamethylditin in the presence of a palladium catalyst with heating in a solvent such as 1,4-dioxane to provide dihydropyridines of general formula (4). The conversion of compounds of general formula (1) to compounds of general formula (4) may require the presence of di-tert-butyl dicarbonate. Dihydropyridines of general formula (4) can be treated with N-chlorosuccinimide and an appropriate source of $^{125}$I such as Na$^{125}$I in the presence of a mixture of acetic acid and methanol to provide [$^{125}$I]dihydropyridines of general formula (3).

Schemes 3–24 illustrate intermediates and/or methods that can be used for generating dihydropyridines of general formula (1). Dihydropyridines of general formula (1) can be processed as described in Scheme 1 or Scheme 2 to generate [$^{125}$I]dihydropyridines of general formula (3).

Scheme 2

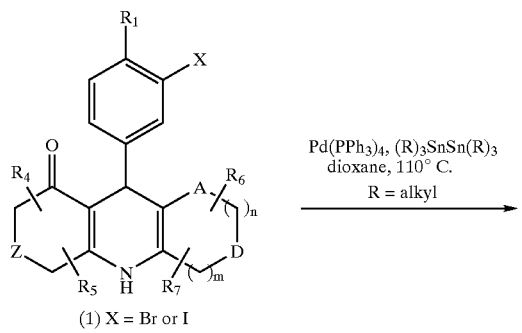

(1) X = Br or I

Pd(PPh$_3$)$_4$, (R)$_3$SnSn(R)$_3$
dioxane, 110° C.
R = alkyl

Scheme 3

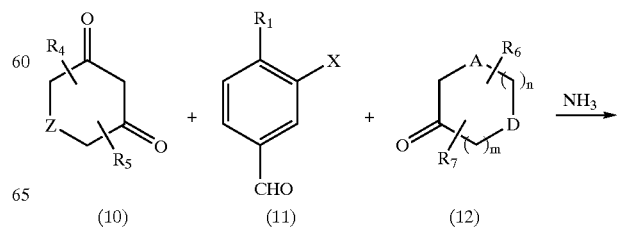

(10) + (11) + (12) → NH$_3$

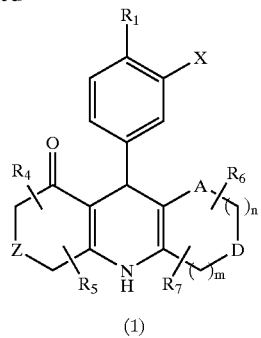

Dihydropyridines of general formula (1), wherein A, D, Z, $R_1$, $R_4$, $R_5$, $R_6$, $R_7$, m and n are as defined in formula (I), and X is Br or I, can be prepared as described in Scheme 3. Dicarbonyl compounds of general formula (10), aldehydes of general formula (11), and carbonyl compounds of general formula (12) can be combined in the presence of ammonia with heating in a solvent such as ethanol to provide dihydropyridines of general formula (1). An additional heating step, with an acid such as HCl, may be required to drive the reaction to completion.

Mixtures of isomers, that result from the synthetic methodology described in Scheme 3 as well as isomers generated in the Schemes that follow, can be separated by methods known to those skilled to the art.

Scheme 4

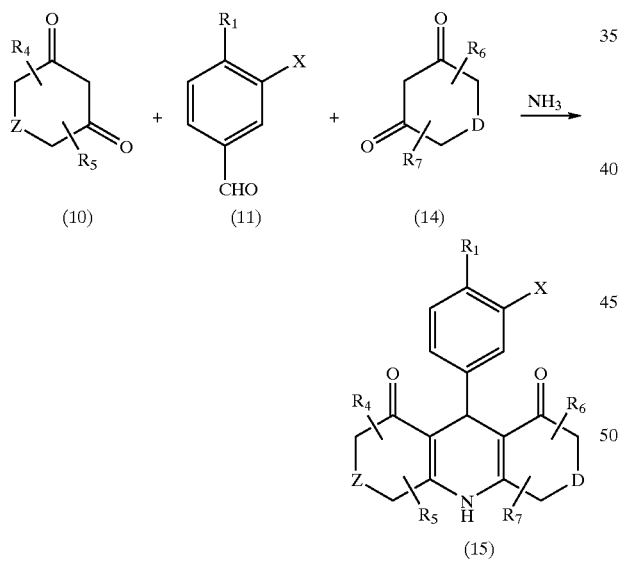

Dihydropyridines of general formula (15), wherein D, Z, $R_1$, $R_4$, $R_5$, $R_6$ and $R_7$ are as defined in formula (I), wherein X is selected from Br or I, can be prepared as described in Scheme 4. One of the dicarbonyl components (10) or (14) can be treated with ammonia followed by addition of aldehydes of general formula (11) and the other dicarbonyl compound (10) or (14) with heating to provide dihydropyridines of general formula (15). An additional heating step, with an acid such as HCl, may be required to drive the reaction to completion.

Scheme 5

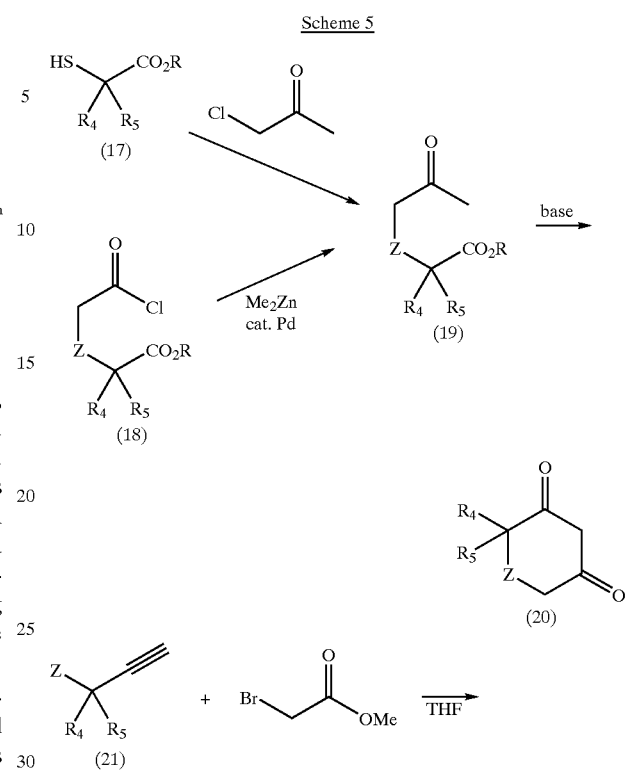

Dicarbonyl compounds of general formula (20), wherein $R_4$, $R_5$, and Z are as defined in formula (I), can be prepared as described in Scheme 5. Esters of general formula (17) can be alkylated with chloroacetone to provide ketoesters of general formula (19) wherein Z is sulfur. Ketoesters of general formula (19) can be cyclized in the presence of a base such as potassium tert-butoxide to provide dicarbonyl compounds of general formula (20). An alternative method of preparing ketoesters of general formula (19) can also be used. Acid chlorides of general formula (18), wherein Z is oxygen, prepared as described in (Terasawa, *J. Org. Chem.* (1977), 42, 1163–1169), can be treated with dimethyl zinc in the presence of a palladium catalyst in a solvent such as diethyl ether or tetrahydrofuran or toluene or a combination thereof to provide ketoesters of general formula (19).

An alternative method of preparing dicarbonyl compounds of general formula (20) can be used as described in Scheme 5. Alkynes of general formula (21) can be treated with methyl bromoacetate to provide compounds of general formula (22). A base such as sodium hydride may be necessary. Alkynes of general formula (22) can be treated with a catalyst such as mercuric acetate in the presence of a catalytic amount of sulfuric acid with heating in a solvent such as methanol followed by treatment with aqueous acid to provide methyl ketones of general formula (23). Methyl ketones of general formula (23) can be treated with a base such as potassium tert-butoxide to provide dicarbonyl compounds of general formula (20).

Alkynes of general formula (21), wherein Z is oxygen, can be purchased or prepared by reaction of a nucleophilic source of acetylene such a ethynylmagnesium bromide or lithium acetylide with an appropriate ketone or aldehyde.

Chiral alkynes of general formula (21), wherein Z is oxygen, can also be purchased or generated by known methods (Midland, M. Tetrahedron (1984), 40, 1371–1380; Smith, R. J.Med.Chem. (1988), 31, 1558–1566) and then processed to provide chiral dicarbonyl compounds of general formula (20).

Dicarbonyl compounds of general formula (20) may also be prepared using the procedures described in (Terasawa, T., Journal of Organic Chemistry 42 (1977)1163); Fehnel, J.Amer.Chem.Soc., (1955), 77, 4241–4242; Morgan, J.Amer.Chem.Soc. (1957), 79, 422; and Er, Helv.Chim.Acta, (1992), 75, 2265–2269).

Scheme 6

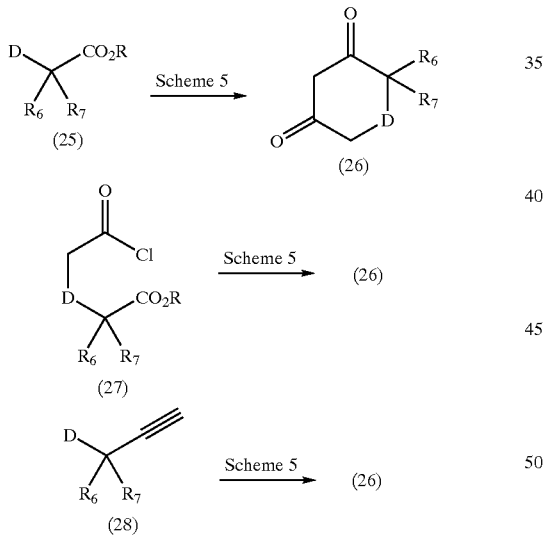

Dicarbonyl compounds of general formula (26), wherein $R_6$ and $R_7$ are defined as in formula (I) and D is selected from oxygen and sulfur, can be prepared as described in Scheme 6. Compounds of general formulas (25), (27) and (28) can be processed as described in Scheme 5 to provide dicarbonyl compounds of general formula (26).

Scheme 7

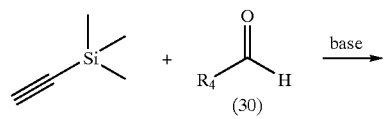

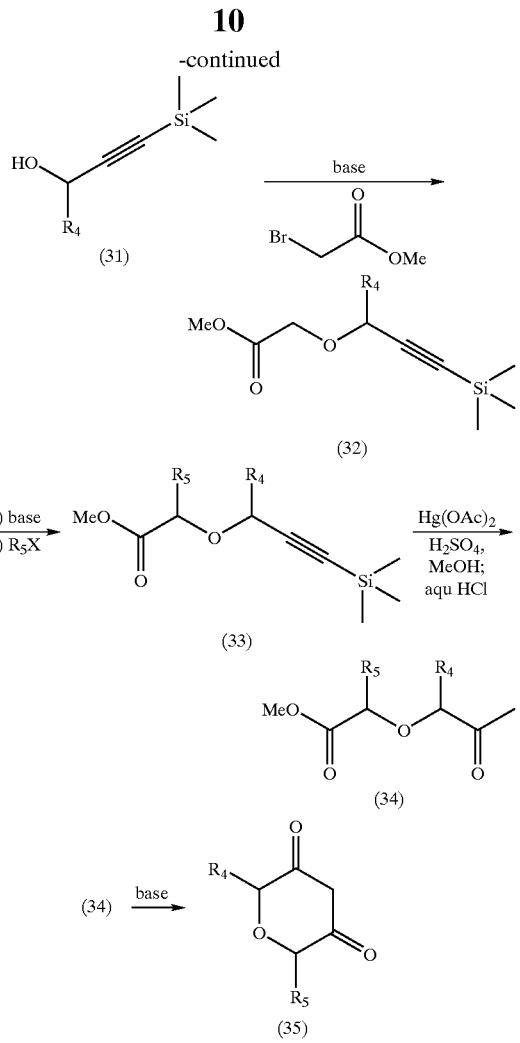

Dicarbonyl pyrans of general formula (35), wherein $R_4$ and $R_5$ are as defined in formula (I), can be prepared as described in Scheme 7. (Trimethylsilyl)acetylene can be deprotonated with a base such as n-butyllithium, methyllithium or ethyl magnesium bromide in a sovent such as diethyl ether or tetrahydrofuran and then treated with an aldehyde of general formula (30) to provide propargyl alcohols of general formula (31). Propargyl alcohols of general formula (31) can be treated with a base such as sodium hydride and then treated with methyl bromoacetate in a solvent such as tetrahydrofuran to provide alkynes of general formula (32). Alkynes of general formula (32) can be treated with a base such as lithium diisopropylamide or lithium bis(trimethylsilyl)amide and then treated with an alkylating agent such as an alkyl halide, alkyl sulfonate or the like in a solvent such as tetrahydrofuran to provide alkynes of general formula (33). Alkynes of general formula (33) can be treated with a source of mercury(II) such as mercury(II) acetate in the presence of acid in a solvent such as methanol followed by treatment with aqueous acid to provide methyl ketones of general formula (34). Methyl ketones of general formula (34) can be treated with a base such as potassium tert-butoxide to provide dicarbonyl pyrans of general formula (35).

Propargyl alcohols of general formula (31) can be separated into single enantiomers as described in (Burgess, J. Amer. Chem. Soc. (1990), 112, 7434–7435; Burgess, J. Amer. Chem. Soc. (1991), 113, 6129–6139; Takano, Synthesis (1993), 12, 1253–1256; and Allevi, Tetrahedron Assymmetry (1997), 8, 93–100). Single enantiomers of general formula (31) can be processed as described in Scheme 7 to provide enantiomerically pure dicarbonyl pyrans of general formula (35).

Scheme 8

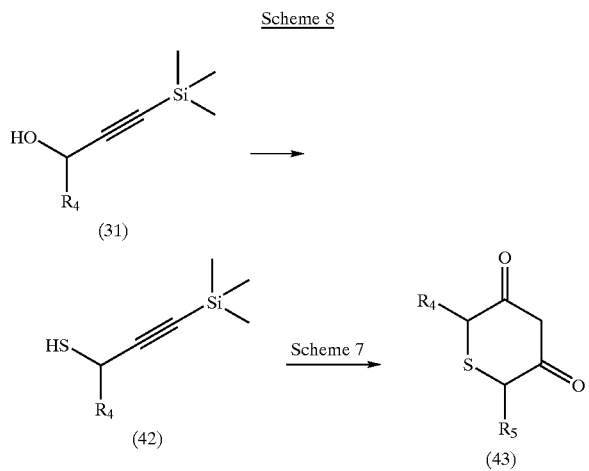

Dicarbonyl thiopyrans of general formula (43), wherein $R_4$ and $R_5$ are as defined in formula (I), can be prepared as described in Scheme 8. Propargyl alcohols of general formula (31) can be converted to the corresponding chlorides using chlorinating agents well known to those of skill in the art such as phosphorous oxychloride and then treated with a source of sulfur such as sodium hydrogen sulfide to provide thiols of general formula (42) as described in (Komasov, Bull. Acad. Sci. USSR Div. Chem. Sci. (Engl. Trans.) (1963), 81–85). Thiols of general formula (42) can be processed as described in Scheme 7 to provide dicarbonyl thiopyrans of general formula (43).

Alternatively, dicarbonyl compounds of general formula (43) may be prepared using procedures as described in (Bergel, Nature(London) (1945), 155, 481).

Scheme 9

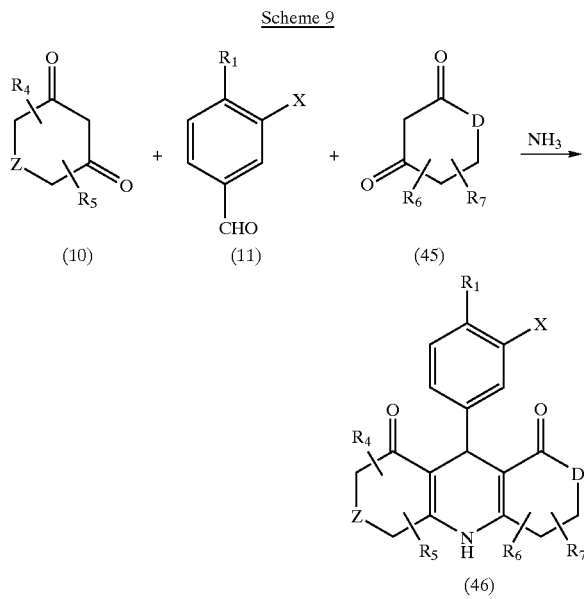

Dihydropyridines of general formula (46), wherein D, Z, $R_1$, $R_4$, $R_5$, $R_6$ and $R_7$ are as defined in formula (I), wherein X is selected from Br or I, can be prepared as described in Scheme 9. One of the dicarbonyl components (10) or (45) can be treated with ammonia followed by addition of aldehydes of general formula (11) followed by treatment with the other dicarbonyl compound (10) or (45) with heating in a solvent such as ethanol to provide dihydropyridines of general formula (46). An additional heating step, with an acid such as HCl, may be required to drive the reaction to completion. Dicarbonyl compounds of general formula (45) can be prepared as described in (d'Angelo, Tett. Lett. (1991), 32, 3063–3066; Nakagawa, Heterocycles (1979), 13, 477–495; Sato, Masayuki, Tetrahedron: Asymmetry (1994), 5, 1665–1668; Sato, Masayuki, Tetrahedron Lett. (1990), 31, 7463–7466; Arnett, Edward M., J.Amer.Chem.Soc. (1987), 109, 809–812; Tabuchi, Hiroyasu, J.Chem.Soc.Perkin Trans.1 (1994), 125–134; Tabuchi, Hiroyasu, J.Org.Chem. (1994), 59, 4749–4759; Hofer, Roger, Helv.Chim.Acta (1985), 68, 969–974).

Scheme 10

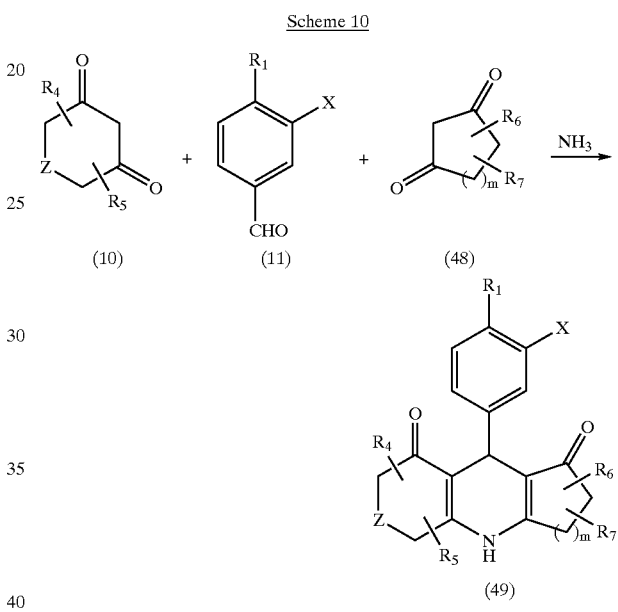

Dihydropyridines of general formula (49), wherein Z, $R_1$, $R_4$, $R_5$, $R_6$, $R_7$ and m are as defined in formula (I) and X is selected from Br or I, can be prepared as described in Scheme 10. One of the dicarbonyl components (10) or (48) can be treated with ammonia followed by addition of aldehydes of general formula (11) and the other dicarbonyl compound (10) or (48) with heating in a solvent such as ethanol to provide dihydropyridines of general formula (49). An additional heating step, with an acid such as HCl, may be required to drive the reaction to completion. Dicarbonyl compounds of general formula (48) can be purchased commercially or prepared using procedures similar to those described in (Stetter, Chem.Ber. (1958), 91, 374; Schinzer, Liebigs Ann.Chem.(1992), 2, 139–144; Knoevenagel, Chem.Ber.(1902), 35, 2182; Champagne, Can.J.Chem., (1964), 42, 212–222; Gilling, J.Chem.Soc. (1913), 103, 2033; Crossley, J.Chem.Soc.(1915), 107, 605; Kvita, Collect.Czech.Chem.Commun.(1957) 22, 1064; Hinkel, J.Chem.Soc.(1931), 814; Fadda, J.Indian Chem.Soc. (1990), 67, 915–917; Craig, J.Org.Chem.(1967), 32, 3743–3749; Deno, J.Amer.Chem.Soc. (1968), 90, 4085–4088; Matoba, Chem.Pharm.Bull.(1983), 2955–2956; Edafiogho, J.Med.Chem.(1992), 2798–2805; Berry, Nicola M. Synthesis (1986), 6, 476–480; Zenyuk, A. A. Chem.Nat.Compd. (Engl.Transl.) (1991), 27, 400–403; Mukheijee, Indian J.Chem.Sect.B (1984), 23, 193–198; Zenyuk, A. A., J.Org.Chem.USSR (Engl.Transl.) (1990), 26, 1926–1927; Demir, Tetrahedron Lett, (1989), 30, 1705–1708; Hamer, Tetrahedron Lett. (1986), 27, 2167–2168; Demir, J.Prakt.Chem./Chem.-Ztg. (1997), 339, 553–563; Rothstein, J.Chem.Soc. (1926), 2017; Landesberg, J.Org.Chem.(1968), 33, 3374–3382; Nilsson, Acta Chem.Scand.Ser.B (1981), 35, 667–668).

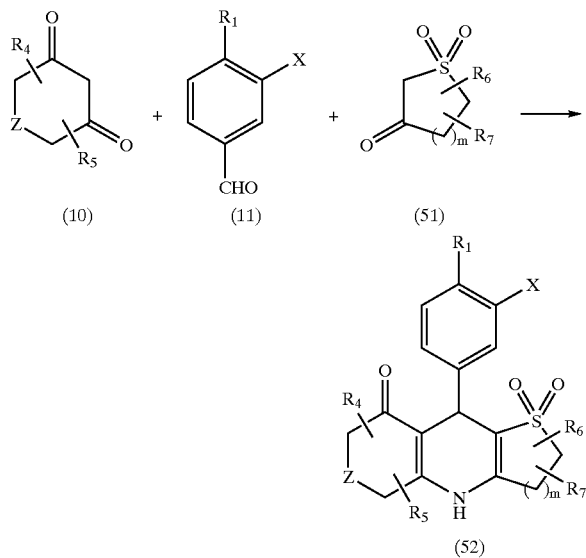

Dihydropyridines of general formula (52), wherein Z, $R_1$, $R_4$, $R_5$, $R_6$, $R_7$ and m are as defined in formula (I) and X is selected from Br or I, can be prepared as described in Scheme 11. Dicarbonyl compounds of general formula (10) can be treated with ammonia, followed by addition of (11) and ketosulfone (51) with heating in a solvent such as ethanol to provide dihydropyridines of general formula (52). An additional heating step, with an acid such as HCl, may be required to drive the reaction to completion.

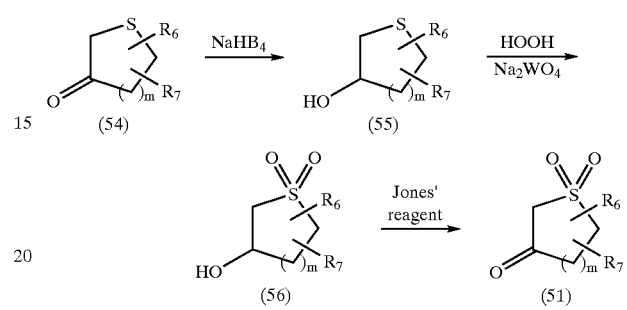

Ketosulfones of general formula (51), wherein $R_6$, $R_7$ and m are as defined in formula (I), can be prepared as described in Scheme 12. Ketones of general formula (54) can be treated with sodium borohydride (or the like) in a solvent such as ethanol to provide alcohols of general formula (55) which can be oxidized to the corresponding sulfone (56) using an oxidizing agent such as hydrogen peroxide catalyzed by sodium tungstate. Sulfones of general formula (56) can be treated with Jones' reagent or the like to provide ketosulfones of general formula (51).

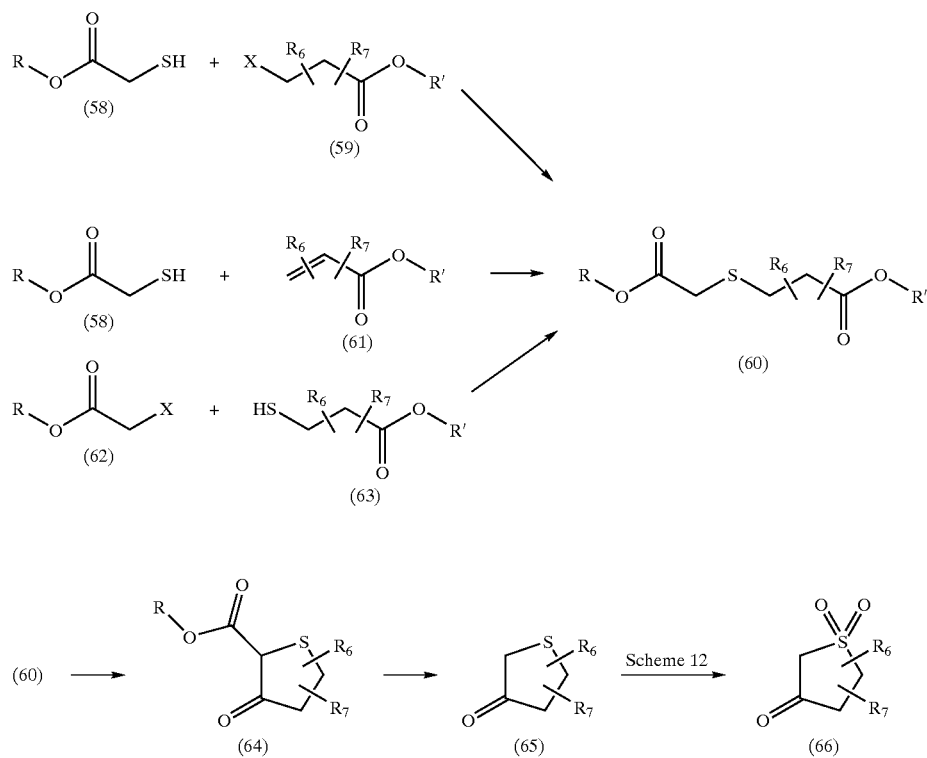

Ketosulfones of general formula (66), wherein $R_6$ and $R_7$ are as defined in formula (I), can be prepared as described in Scheme 13. Thiols of general formula (58) wherein R is H or lower alkyl, can be reacted with an alkyl halide of general formula (59), wherein R' is H or lower alkyl to provide a sulfide of general formula (60), wherein R is H or lower alkyl, as described in (Fredga, Ark.Kemi (1943), 16 B, 8, 5; Challenger, J.Chem.Soc. (1959), 61, 68; Schoeberl, Justus Liebigs Ann. Chem.(1956), 599, 140, 151; Acheson, J.Chem.Soc.(1961), 650–660; Ghosh, J.Med.Chem. (1994), 37, 1177–1188). Sulfides of general formula (60) are also available via reaction between thiols of general formula (58) and unsaturated acids or esters of general formula (61) as described in (Reinhoudt, Synthesis, (1978) 368–370; Schoeberl, Justus Liebigs Ann. Chem.(1956), 599, 140, 151; Martani, Ric.Sci.(1959) 29, 520, 523; Dowd, Tetrahedron (1991), 47, 4847–4860; Fiesselmann, Chem.Ber.(1954), 87, 848, 854; Ranu, Tetrahedron (1992), 48, 1327–1332; Binder, Arch.Pharm.(Weinheim Ger.)(1981), 314, 557–564). A third method of generating sulfides of general formula (60) is via reaction of a thiol of general formula (63) wherein R' is H or lower alkyl, with an alkylhalide of general formula (62), wherein R is H or lower alkyl, as described in (Larsson, Chem.Ber. (1934), 67, 759; Kato, Chem.Pharm.Bull.(1986), 34, 486–495).

Sulfides of general formula (60) can be cyclized to provide sulfides of general formula (64) in the presence of a Lewis acid such as titanmium tetrachloride or a base such as sodium metal or an alkoxide. Examples of this transformation can be found in (Duus, Tetrahedron (1981), 37, 2633–2640; Deshmukh, Synth.Commun.(1996), 26, 1657–1662; Avison, Nature(London) (1944), 154, 459).

Sulfides of general formula (64) can be decarboxylated to provide sulfides of general formula (65) preferably in the presence of aqueous acid. Examples of this transformation can be found in (Ghosh, J.Med.Chem.(1994), 37, 1177–1188; Larsson, Sven.Kem.Tidskr.(1945), 57, 248; Woodward, J.Amer.Chem.Soc.(1946), 68, 2229, 2234). Sulfides of general formula (65) can be processed as described in Scheme 12 to provide ketosulfones of general formula (66).

Scheme 14

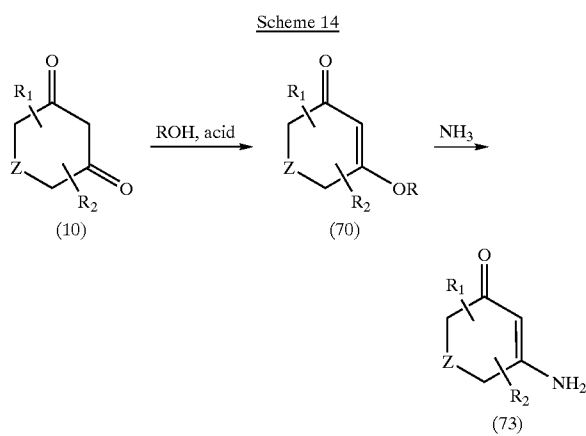

Enaminones of general formula (73), wherein Z, $R_1$ and $R_2$ are as defined in formula (I), can be prepared as described in Scheme 14. Dicarbonyl compounds (10) can be treated with an alcohol such as ethyl alcohol in the presence of an acid catalyst such as para-toluenesulfonic acid to provide vinyl ethers of general formula (70), wherein R is lower alkyl such as ethyl. Vinyl ethers of general formula (70) may contain a mixture of isomers which can be separated by a separatory method such as chromatography. Vinyl ethers of general formula (13) can be treated with ammonia in a solvent such as methanol to provide enaminones of general formula (73).

Scheme 15

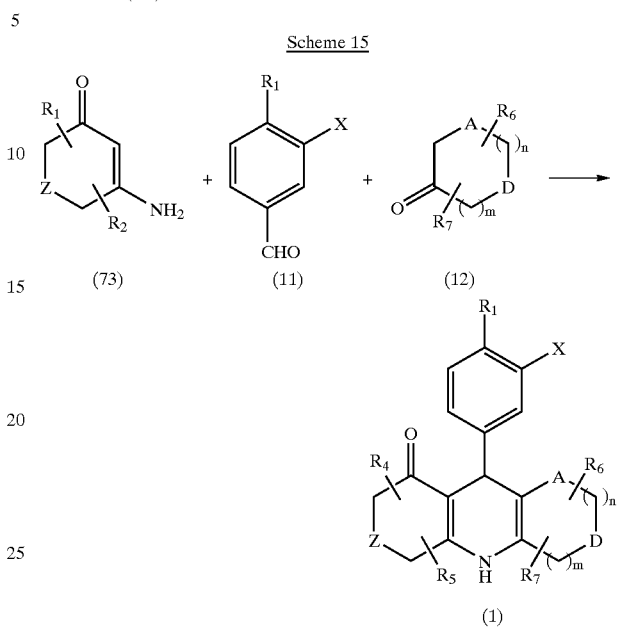

Dihydropyridines of general formula (1), wherein A, D, Z, $R_1$, $R_4$, $R_5$, $R_6$, $R_7$, m and n are as defined in formula (I) and X is Br or I, can be prepared as described in Scheme 15. Enaminones of general formula (73) can be treated with aldehydes of general formula (11) and carbonyl compounds of general formula (12) with heating in a solvent such as ethanol to provide dihydropyridines of general formula (1). An additional heating step, with an acid such as HCl, may be required to drive the reaction to completion.

Scheme 16

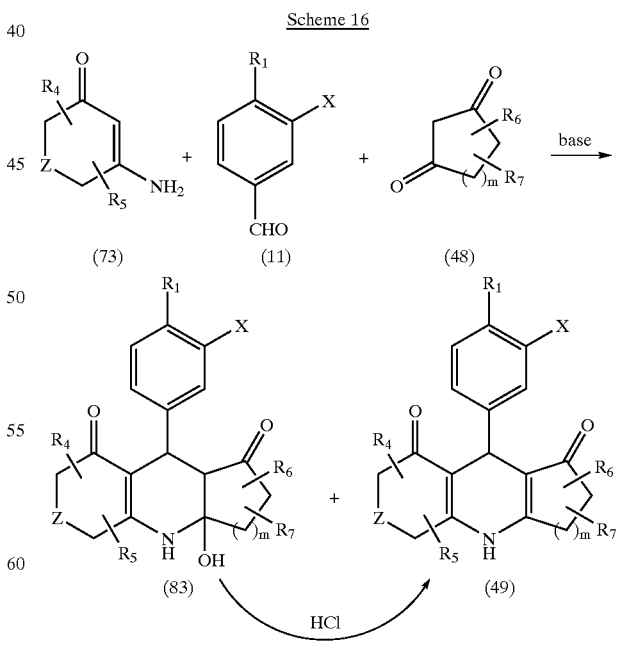

Dihydropyridines of general formula (49), wherein Z, $R_1$, $R_4$, $R_5$, $R_6$, $R_7$ and m are as defined in formula (I) and X is selected from Br or I, can be prepared as described in Scheme 16. Enaminones of general formula (73) can be treated with aldehydes (11) and dicarbonyl compounds of general formula (48) with heating in a solvent such as ethanol in the presence of a base such as triethylamine to provide hemiaminals of general formula (83), dihydropyridines of general formula (49), or mixtures thereof. Hemiaminals (83) and mixtures containing hemiaminals (83) and dihydropyridines (49) may be treated with heat in the presence of an acid such as HCl in a solvent such as ethanol to effect complete conversion to dihydropyridines of general formula (49).

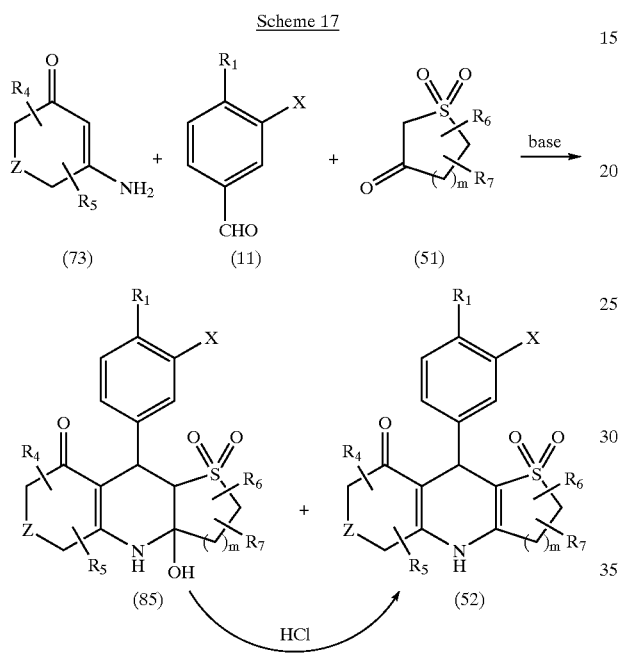

Scheme 17

An alternate method of preparing dihydropyridines of general formula (52), wherein Z, $R_1$, $R_4$, $R_5$, $R_6$, $R_7$ and m are as defined in formula (I) and X is selected from Br or I, can be used as described in Scheme 17. Enaminones of general formula (73) can be treated with aldehydes of general formula (11) and ketosulfones of general formula (51) with heating in a solvent such as ethanol in the presence of a base such as triethylamine to provide hemiaminals of general formula (85), dihydropyridines of general formula (52), or mixtures thereof. Hemiaminals (85) and mixtures containing hemiaminals (85) and dihydropyridines (52) may be treated with heat in the presence of an acid such as HCl in a solvent such as ethanol to effect complete conversion to dihydropyridines of general formula (52).

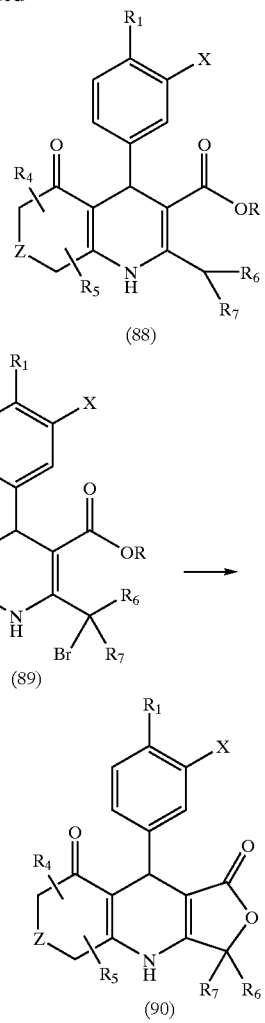

Dihydropyridines of general formula (90), wherein Z, $R_1$, $R_4$, $R_5$, $R_6$ and $R_7$ are as defined in formula (I) and X is Br or I, can be prepared as described in Scheme 18. Enaminones of general formula (73) can be treated with aldehydes of general formula (11) and β-ketoesters of general formula (87), wherein R is lower alkyl, to provide dihydropyridines of general formula (88). Dihydropyridines of general formula (88) can be treated with brominating agents such as N-bromosuccinimide or pyridinium tribromide in a solvent such as methanol, ethanol, isopropanol, or chloroform to provide dihydropyridines of general formula (89). Dihydropyridines of general formula (89) can be heated neat or heated in a solvent such as chloroform to provide dihydropyridines of general formula (90).

Scheme 18

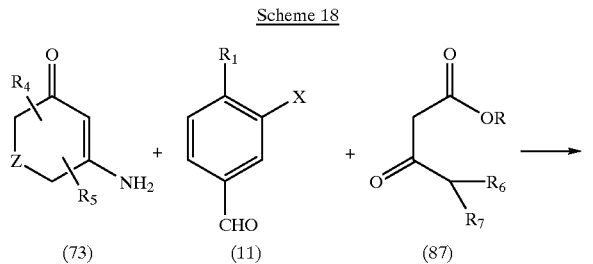

Scheme 19

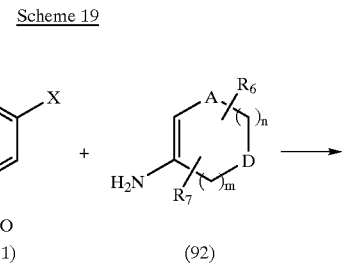

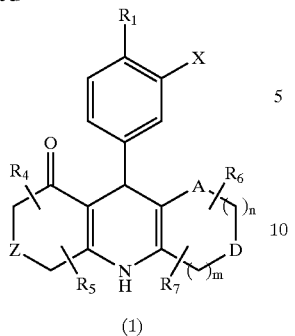

(1)

An alternate method of preparing dihydropyridines of general formula (I), wherein A, D, Z, $R_1$, $R_4$, $R_5$, $R_6$, $R_7$, m and n are as defined in formula (I) and X is Br or I, is described in Scheme 19. Dicarbonyl compounds of general formula (10) can be treated with aldehydes of general formula (11) and enamines of general formula (92) with heating in a solvent such as ethanol to provide dihydropyridines of general formula (1). An additional heating step, with an acid such as HCl, may be required to drive the reaction to completion.

Scheme 20

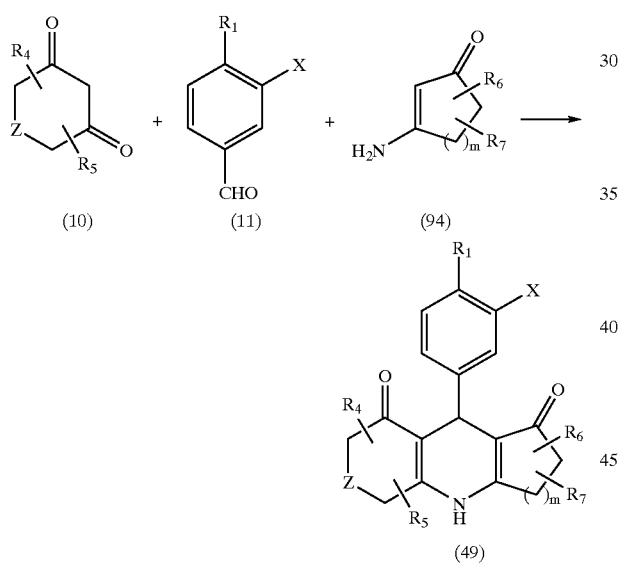

An alternate method of preparing dihydropyridines of general formula (49), wherein Z, $R_1$, $R_4$, $R_5$, $R_6$, $R_7$ and m are as defined in formula (I) and X is Br or I, is described in Scheme 20. Dicarbonyl compounds of general formula (10) can be treated with aldehydes of general formula (11) and aminocycloalkenones of general formula (94) with heating in a solvent such as ethanol to provide dihydropyridines of general formula (49). An additional heating step, with an acid such as HCl, may be required to drive the reaction to completion. Aminocycloalkenones, such as 3-amino-2-cyclohexene-1-one, of general formula (94) can be purchased commercially (Fluka Chemical, Milwaukee, Wis.) or prepared as described in Kikani, B. Synthesis, (1991), 2, 176. Aminocycloalkenones of general formula (94) may also be prepared by treating dicarbonyl compounds of general formula (48) with ammonia in a solvent such as methanol.

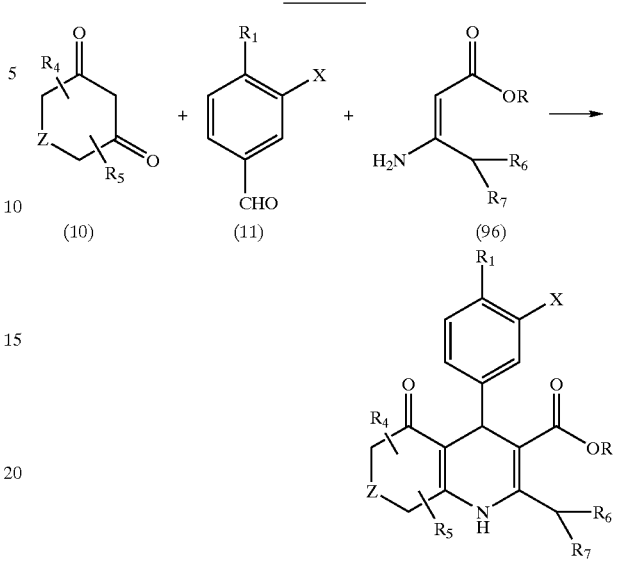

An alternate method of preparing dihydropyridines of general formula (90), wherein Z, $R_1$, $R_4$, $R_5$, $R_6$, and $R_7$ are as defined in formula (I) and X is Br or I, is described in Scheme 21. Diones of general formula (10) can be treated with aldehydes of general formula (11) and compounds of general formula (96), wherein R is lower alkyl, to provide dihydropyridines of general formula (88) which can be processed as described in Scheme 18 to provide dihydropyridines of general formula (90). Compounds of general formula (96) can be generated from the reaction of β-ketoesters of general formula (87) as described in Scheme 18 with ammonia.

Scheme 22

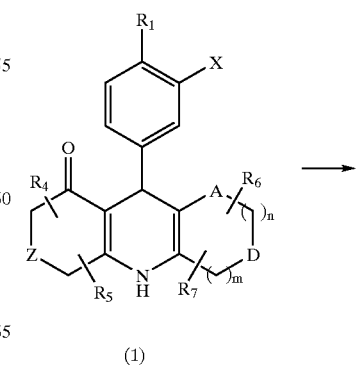

(1)

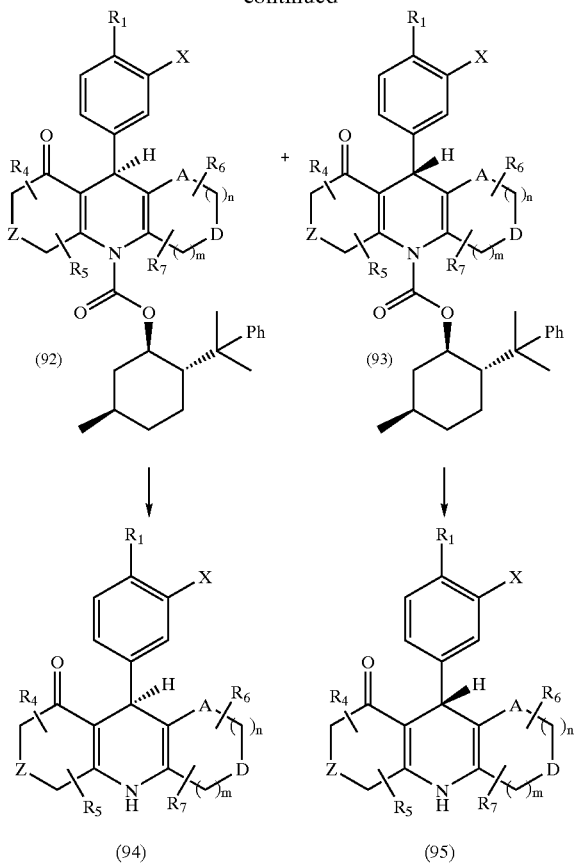

(92) (93)

(94) (95)

Enantiomers of general formula (94) and (95), wherein A, D, Z, $R_1$, $R_4$, $R_5$, $R_6$, $R_7$, m and n are as defined in formula (I) and X is Br or I, may be prepared as single enantiomers by the method illustrated in Scheme 22. Dihydropyridines of general formula (1) can be treated with a base such as potassium tert-butoxide and (−)-8-phenylmenthol chloroformate in a solvent such as tetrahydrofuran to provide a mixture of diastereomeric carbamates (92) and (93). Diastereomers (92) and (93) can be separated by separatory methods known to those skilled in the art such as column chromatography over silica gel. The individual carbamates (92) and (93) following separation can be treated with sodium methoxide in methanol to produce the single enantiomers (94) and (95) respectively.

In addition to the methods illustrated in Scheme 22, racemic compounds of general formula (1) may be separated into individual enantiomers by chiral chromatography. Also, enantiomerically pure intermediates may be carried through Schemes 1–21 to provide enantiomerically pure [$^{125}$I] dihydropyridines of general formula (3). For example, individual enantiomers may be synthesized from chiral diones of general formula (10).

Many of the starting benzaldehydes necessary to carry out the methods described in the preceeding and following Schemes may be purchased from commercial sources or may be synthesized by known procedures found in the chemical literature. Appropriate literature references for the preparation of benzaldehydes may be found in the following section or in the Examples. For starting materials not previously described in the literature the following Schemes are intended to illustrate their preparation through a general method.

The preparation of benzaldehydes used to synthesize compounds of the invention may be found in the following literature references: Pearson, Org. Synth. Coll. Vol V (1973), 117; Badder, J. Indian Chem. Soc. (1976), 53, 1053; Hodgson, J. Chem. Soc. (1927), 2425.

Scheme 23

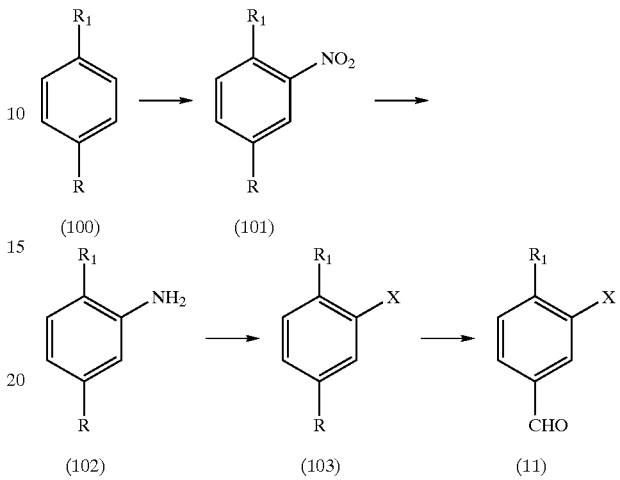

(100)  (101)

(102)  (103)  (11)

Aldehydes of general formula (11), wherein $R_1$ is as defined in formula (I) and X is selected from Br or I, can be prepared according to the method described in Scheme 23. A para substituted compound of general formula (100) wherein R is COOH, CHO, $CH_2OH$ or COOR', wherein R' is lower alkyl, may by nitrated to provide compounds of general formula (101). Nitration on compounds of general formula (100) are well known to those skilled in the art. Nitrated compounds of general formula (101) can be reduced to the corresponding anilines of general formula (102) using methods known to those skilled in the art. Anilines of general formula (102) can be converted to bromides and iodides of general formula (103) using the Sandmeyer reaction. The Sandmeyer reaction involves converting anilines of general formula (102) to an intermediate diazonium salt with sodium nitrite. The diazonium salts can be treated with an appropriate source of bromine or iodine to provide the bromide or iodide. The Sandmeyer reaction and conditions for effecting the transformation are well known to those skilled in the art of organic chemistry. Compounds of general formula (103) can be converted to aldehydes of general formula (11) using reductive (reduce ester or acid) or oxidative (oxidize alcohol) procedures well known to those skilled in the art.

Scheme 24

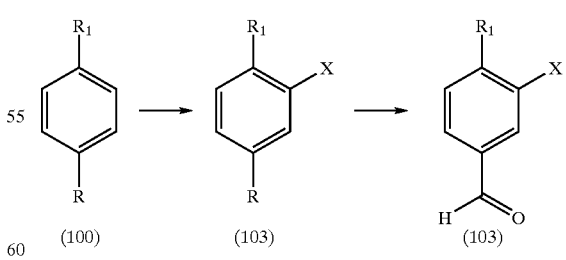

(100)  (103)  (103)

Aldehydes of general formula (11), wherein $R_1$ is as defined in formula (I) and X is selected from Br or I, can also be prepared according to the method described in Scheme 24. A para substituted compound of general formula (100) wherein R is COOH, CHO, $CH_2OH$ or COOR', wherein R' is lower alkyl, may by subjected to conditions of an electrophilic aromatic substitution reaction to provide bromides or iodides of general formula (103). Compounds of general formula (103) can be converted to aldehydes of general formula (11) using reductive (reduce ester or acid) or oxidative (oxidize alcohol) reductive (reduce ester or acid) or oxidative (oxidize alcohol)procedures well known to those skilled in the art.

EXAMPLE 1

9-(4-fluoro-3-[I$^{125}$]iodophenyl)-2,3,5,9-tetrahydro-4H-pyrano[3,4-b]thieno[2,3-e]pyridin-8(7H)-one 1,1-dioxide

EXAMPLE 1A methyl (2-propynyloxy)acetate

A mechanically stirred suspension of sodium hydride (60 5% dispersion in mineral oil) (50 g, 1.25 mol) in tetrahydrofuran (800 mL) at 0° C. under nitrogen was treated dropwise with a solution of propargyl alcohol (84 g, 1.5 mol) in tetrahydrofuran (175 mL), stirred at 0° C. for 1 hour, treated with a solution of methyl bromoacetate in tetrahydrofuran (250 mL) over 15 minutes, stirred at 0° C. for 30 minutes, stirred at ambient temperature for 2 hours, and treated with 2M HCl (800 mL). The organic layer was isolated and the aqueous layer was extracted with ethyl acetate (2×, 500 mL). The combined organic layers were washed with brine (200 mL), dreid (MgSO4), filtered, concentrated and distilled (bp 75–85° C. at 20 torr) to provide the title compound (83 g).

$^1$H NMR (CDCl$_3$) δ2.49 (t, 1H), 3.77 (s, 3H), 4.22 (s, 2H), 4.32 (d, 2H).

EXAMPLE 1B methyl (2-oxopropoxy)acetate

The product from Example 1A (56 g, 0.44 mol) in methanol (1.5 L) was treated with mercury(II) acetate (14 g, 44 mmol), treated with concentrated sulfuric acid (3 mL), refluxed for 1 hour, allowed to cool to ambient temperature, concentrated to a volume of 200 mL, treated with 1M HCl (500 mL) and extracted with dichloromethane (thrice, 300 mL). The combined dichloromethane layers were dried (MgSO4), filtered, concentrated and distilled (65–95° C. at 1 torr) to provide the title compound.

$^1$H NMR (CDCl$_3$) δ2.18 (2, 3H), 3.77 (s, 3H), 4.20 (s, 2H), 4.21 (s, 2H).

EXAMPLE 1C 2H-pyran-3,5(4H,6H)-dione

The product from Example 1B (50. g, 0.34 mol) in anhydrous ether (1.0 L) was added dropwise over 2 hours to a mechanically stirred solution of 1M potassium tert-butoxide (in tert-butanol, 340 mL) in anhydrous ether (500 mL). The mixture was treated with 1M HCl (200 mL) and the layers were separated. The aqueous layer was extracted with ethyl acetate (twice, 500 mL). The combined organic layers were washed with brine (2×100 mL), dried (MgSO$_4$), filtered and concentrated (keeping the bath temperature below 30° C.). This crude product which crystallized on standing was treated with 1:1 hexane:ethyl acetate (200 mL). The crystals were collected by filtration, washed with 1:1 hexane:ethyl acetate (100 mL) and dried under vacuum to provide the title compound (12.2 g), (Terasawa, J. Org. Chem. (1977), 42, 1163–1169).

$^1$H NMR (DMSO-d$_6$) δ4.07 (s, 4H), 5.32 (s, 1H), 11.9 (bs, 1H).

EXAMPLE 1D 5-amino-2H-pyran-3(6H)-one

The crude product from Example 1C (33 g) was treated with ethanol (800 mL) and concentrated sulfuric acid (0.2 mL), heated to reflux for 2 hours, cooled to 0° C., treated with methanol saturated with ammonia (200 mL), stirred at ambient temperature for 4 hours and concentrated. The residue was purified by flash chromatography over silica gel (2% and then 5% and then 10% methanol/methylene chloride) to provide the title compound (5 g).

MS (DCI/NH$_3$) m/z 114 (M+H)$^+$, 131 (M+NH$_4$)$^+$;

$^1$H NMR (DMSO-d$_6$) δ3.80 (s, 2H), 4.19 (s, 2H), 5.01 (s, 1H), 7.01 (bs, 2H).

EXAMPLE 1E 9-(3-bromo-4-fluorophenyl)-2,3,5,9-tetrahydro-4H-pyrano[3,4-b]thieno[2,3-e]pyridin-8(7H)-one 1,1-dioxide A mixture of the product from Example 1D (1.5 g, 13 mmol), 3-bromo-4-fluorobenzaldehyde (3.2 g, 16 mmol), tetrahydrothiophene-3-oxo-1,1-dioxide (1.8 g, 13 mmol) and triethylamine (0.93 mL, 6.6 mmol) in ethanol (20 mL) were stirred in a sealed tube at 80° C. for 60 hours, cooled and concentrated to dryness. The residue was treated with ethanol (50 mL), treated with 1M HCl (in diethyl ether, 5 mL), heated to reflux for 5 minutes and kept at ambient temperature for 3 hours. The resulting solid was collected by filtration, washed with ethanol and dried under vacuum for 16 hours to provide the title compound (3.2 g).

mp>260° C.;

MS (ESI(+)) m/z 414 (M+H)$^+$, 431 (M+NH$_4$)$^+$;

MS (ESI(−)) m/z 412 (M−H)$^-$;

$^1$H NMR (DMSO-d$_6$) δ2.85 (m, 1H), 3.08 (m, 1H), 3.33–3.42 (m, 2H), 4.03 (s, 2H), 4.49 (AB q, 2H), 4.90 (s, 1H), 7.27 (m, 2H), 7.45 (dd, 1H), 10.14 (s, 1H);

Anal. Calcd for C$_{16}$H$_{13}$NO$_4$SFBr: C, 46.39; H, 3.16; N, 3.38. Found: C, 46.25; H, 3.24; N, 3.26.

EXAMPLE 1F (1S,2R,5S)-5-methyl-2-(1-methyl-1-phenylethy)cyclohexyl-9-(3-bromo-4-fluorophenyl)-8-oxo-2,3,5,7,8,9-hexahydro-4H-pyrano[3,4-b]thieno[2,3-e]pyridine-4-carboxylate 1,1-dioxide A suspension of the product from Example 1E (1.58 g, 3.7 mmol) in THF (40 mL) at 0° C. under a nitrogen atmosphere was treated with a 1M solution of potassium tert-butoxide in THF (4.1 mL) dropwise over 5 minutes. The mixture was stirred at ambient temperature for 30 minutes, cooled to 0° C., treated with a solution of (−)-8-phenylmenthol chloroformate (Yamamoto, Y., J.Amer.Chem.Soc., (1992), 114, 121–125) (1.31 g, 4.4 mmol) in THF (20 mL) over 5 minutes, stirred at ambient temperature for 16 hours, diluted with methylene chloride (150 mL) and washed with aqueous sodium bicarbonate (30 mL). The layers were separated and the aqueous layer was extracted with methylene chloride (50 mL). The combined organic layers were dried (MgSO$_4$), filtered and concentrated. The residue was purified by flash chromatography over silica gel (3:2:1 chloroform/hexanes/diethyl ether) to provide the less polar diasteriomer (0.98 g).

MS (ESI(+)) m/z 672 (M+H)$^+$, 689 (M+NH$_4$)$^+$;

MS (ESI(−)) m/z 670 (M−H)$^-$.

EXAMPLE 1G (+)-9-(3-bromo-4-fluorophenyl)-2,3,5,9-tetrahydro-4H-pyrano[3,4-b]thieno[2,3-e]pyridin-8(7H)-one 1,1-dioxide The less polar diastereomer from Example 1F (0.98 g, 1.4 mmol) in methanol/methylene chloride (40 mL/10 mL) was degassed with nitrogen, treated with 25% sodium methoxide in methanol (30 drops), stirred for 16 hours, filtered through a 45 mm syringe filter and concentrated to a volume of 5 mL. The solid which had precipitated was collected by filtration, washed with methanol and dried under reduced pressure for 16 hours to provide the title compound (0.36 g).

$[\alpha]^{23}_D$+117° (DMSO, c 0.925).

MS (ESI(+)) m/z 414 (M+H)$^+$, 431 (M+NH$_4$)$^+$;

MS (ESI(−)) m/z 412 (M−H)$^−$;

$^1$H NMR (DMSO-d$_6$) δ2.85 (m, 1H), 3.08 (m, 1H), 3.33–3.42 (m, 2H), 4.03 (s, 2H), 4.49 (AB q, 2H), 4.90 (s, 1H), 7.27 (m, 2H), 7.45 (dd, 1H), 10.14 (s, 1H);

Anal. Calcd for C$_{16}$H$_{13}$NO$_4$SFBr: C, 46.39; H, 3.16; N, 3.38. Found: C, 46.07; H, 3.02; N, 3.19.

EXAMPLE 1H tert-butyl 9-(3-bromo-4-fluorophenyl)-8-oxo-2,3,5,7,8,9-hexahydro-4H-pyrano[3,4-b]thieno[2,3-e]pyridine-4-carboxylate 1,1-dioxide The product from Example 1G (0.040 g, 0.096 mmol), di-tert-butyl dicarbonate (0.12 g, 0.55 mmol) and 4-dimethylaminopyridine (0.0020 g, 0.016 mmol) in acetonitrile (3 mL) were stirred for 2 hours at ambient temperature and concentrated. The residue was purified by chromatography on silica gel (2:1 and then 1:1 hexanes:ethyl acetate) to provide the title compound (0.035 g) which crystallized on standing.

MS (ESI(+)) m/z 531 (M+NH$_4$)$^+$.

EXAMPLE 1I tert-butyl 9-[4-fluoro-3-(trimethylstannyl)phenyl]-8-oxo-2,3,5,7,8,9-hexahydro-4H-pyrano[3,4-b]thieno[2,3-e]pyridine-4-carboxylate 1,1-dioxide The product from Example 1H (0.035 g, 0.068 mmol) in anhydrous 1,4-dioxane (1 mL) under an atmosphere of nitrogen was treated with hexamethylditin (0.14 mL, 0.5 mmol) and tetrakis(triphenylphosphine)palladium(0) (0.050 g, 0.043 mmol), stirred at 100° C. for 1 hour, allowed to cool to ambient temperature and concentrated. The residue was purified by chromatography on silica gel (3:2 hexanes:ethyl acetate) to provide the title compound (0.031 g) which crystallized on standing.

MS (ESI(+)) m/z 598 (M+H)$^+$.

EXAMPLE 1J 9-(4-fluoro-3-iodophenyl)-2,3,5,9-tetrahydro-4H-pyrano[3,4-b]thieno[2,3-e]pyridin-8(7H)-one 1,1-dioxide The product from Example 1I (0.023 g, 0.038 mmol) in 1% acetic acid in methanol (25 mL) was treated with N-chlorosuccinimide (0.010 g, 0.077 mmol) and sodium iodide (0.011 g, 0.077 mmol), stirred for 10 minutes, treated with pulverized sodium thiosulfate pentahydrate (0.020 g, 0.080 mmol), stirred for 10 minutes and concentrated to dryness. The residue was treated with trifluoroacetic acid (3 mL), stirred at ambient temperature for 15 minutes and concentrated to dryness. The residue was retreated with trifluoroacetic acid (3 mL), heated gently on a steam bath for 1 minute, allowed to cool to ambient temperature and concentrated to dryness. The residue was purified by chromatography on silica gel (2% methanol and then 5% methanol in methylene chloride) to provide the title compound (0.0156 g).

mp>260° C.;

MS (ESI(−)) m/z 460 (M−H)$^−$;

$^1$H NMR (DMSO-d$_6$) δ2.77–2.90 (m, 1H), 3.01–3.14 (m, 1H), 3.32–3.43 (m, 2H), 4.02 (s, 2H), 4.49 (AB q, 2H), 4.87 (s, 1H), 7.16 (t, 1H), 7.24 (m, 1H), 7.59 (dd, 1H), 10.13 (bs, 1H);

Anal. Calcd for C$_{16}$H$_{13}$NO$_4$SFI: C, 41.66; H, 2.84; N, 3.04. Found: C, 41.28; H, 2.79; N, 2.87.

EXAMPLE 1K 9-(4-fluoro-3-[I$^{125}$]iodophenyl)-2,3,5,9-tetrahydro-4H-pyrano[3,4-b]thieno[2,3-e]pyridin-8(7H)-one 1,1-dioxide A solution of methanol (29.4 μL) and acetic acid (0.6 μL) was added to dry sodium [I$^{125}$]iodide (12.44 mCi, 6.22 nmol), the product from Example 1I (25 μg, 41.8 nmol) in methanol (25 μL) and N-chlorosuccinimide (5 μg, 37.4 nmol) in methanol (5 μL). After incubating for 10 minutes, sodium metabisulfate (10 μg, 52.6 nmol) in water (2 μL) was added and the reaction mixture was dried via a stream of nitrogen gas. Trifluoroacetic acid (50 μL) was added and the mixture was heated at 65° C. for 2 minutes. The mixture was allowed to cool to ambient temperature and the solvents removed via a stream of nitrogen. The title compound was purified by reversed-phase HPLC (4 mm×250 mm C18 column, eluting with 5% acetonitrile in water to 90% acetonitrile in water over a 30 minute period, both acetonitrile and water phases contained 0.1% TFA, 1 mL/minute at 35° C.). 7590 μCi (0.4 mL) was collected at about 18 minutes into ethanol (0.5 mL). The 0.9 mL of ethanol was diluted with additional ethanol (5.0 mL). A portion of this diluted solution (5 μL) was added to water (15 μL) and determined to have one peak, >99.5% radiochemical purity by reversed-phase HPLC (4 mm×50 mm C5 column, eluting with 5% acetonitrile in water to 90% acetonitrile in water, both acetonitrile and water phases contained 0.1% TFA).

EXAMPLE 2

5-(4-fluoro-3-[I$^{125}$]iodophenyl)-5,10-dihydro-1H,3H-dipyrano[3,4-b:4,3-e]pyridine-4,6(7H,9H)-dione

EXAMPLE 2A

3-Amino-4-fluorobenzyl alcohol

3-Amino-4-fluorobenzoic acid (15 g, 97 mmol) in tetrahydrofuran at 0° C. was treated with 1.0M borane-tetrahydrofuran complex (50 mL), stirred overnight at ambient temperature, treated with an additional 130 mL of 1.0M borane-tetrahydrofuran complex, stirred 10 hours, quenched by the addition of methanol, stirred 3 hours at ambient temperature, concentrated and partitioned between aqueous sodium bicarbonate/methylene chloride. The methylene chloride layer was separated, dried (sodium sulfate), filtered, and concentrated. The residue was purified by flash chromatography over silica gel (ethyl acetate:hexanes 1:1) to provide 7.0 g of the title compound.

¹H NMR (CDCl₃) δ4.58 (s, 2H), 6.67 (br m, 1H), 6.81 (d, 1H), 6.95 (t, 1H).

EXAMPLE 2B

4-Fluoro-3-iodobenzylalcohol

The product from Example 2A (7.0 g, 50 mmol) in water (100 mL) at 0° C. was treated slowly with concentrated sulfuric acid (30 mL) at a rate to maintain the temperature below 10° C. and then treated dropwise with an aqueous solution of sodium nitrite (3.45 g, 50 mmol). This solution was then added to a solution of potassium iodide (8.13 g, 50 mmol) in water (15 mL), heated to 60° C. for 2 hours, cooled and extracted with methylene chloride. The methylene chloride layer was washed with 10% sodium hydroxide, washed with 1M sodium thiosulfate, washed with 10% hydrochloric acid, washed with aqueous sodium bicarbonate, dried (sodium sulfate), filtered, and concentrated. The residue was purified by flash chromatography over silica gel (ethyl acetate/hexane 7:3) to provide 6.4 g of the title compound.

¹H NMR (CDCl₃) δ1.69 (t, 1H), 4.66 (d, 2H), 7.05 (t, 1H), 7.60 (d, 1H), 7.78 (dd, 1H).

EXAMPLE 2C

4-Fluoro-3-iodobenzaldehyde

The product from Example 2B (6.4 g, 26 mmol) in chloroform (300 mL) was treated with manganese dioxide (4.5 g, 50 mmol), stirred overnight, treated with an additional portion of manganese dioxide (2.25 g), stirred overnight, filtered and concentrated. The residue was purified by flash chromatography over silica gel (ethyl acetate/hexane 1:4) to provide 1.9 g of the title compound.

¹H NMR (CDCl₃) δ7.23 (t, 1H), 7.89 (m, 1H), 8.32 (dd, 1H), 9.91 (s, 1H).

EXAMPLE 2D 5-(4-fluoro-3-iodophenyl)-5,10-dihydro-1H,3H-dipyrano[3,4-b:4,3-e]pyridine-4,6(7H,9H)-dione The product from Example 1C (0.23 g, 2.0 mmol), the product from Example 2C (0.50 g, 2.0 mmol) and the product from Example 1D (0.23 g, 2.0 mmol) were combined in ethanol (4 mL) and heated at 80° C. in a sealed tube for 60 hours and allowed to stand at ambient temperature for 1 hour. The solid was collected by filtration, washed with ethanol and dried to yield 0.88 g (59%) of the title compound.

mp>260° C.;

¹H NMR (DMSO-d₆) δ4.05 (s, 4H), 4.50 (AB q, 4H), 4.90 (s, 1H), 7.15 (t, 1H), 7.20 (m, 1H), 7.57 (dd, 1H), 10.10 (bs, 1H);

MS (ESI+) m/z 442 (M+H)⁺;

MS (ESI−) m/z 440 (M−H)⁻;

Anal. Calcd for C₁₇H₁₃NO₄FI: C, 46.28; H, 2.97; N, 3.17. Found: C, 46.61; H, 3.11; N, 2.87.

EXAMPLE 2E tert-butyl 5-(4-fluoro-3-iodophenyl)-4,6-dioxo-3,4,5,6,7,9-hexahydro-1H,10H-dipyrano[3,4-b:4,3-e]pyridine-10-carboxylate The product from Example 2D and di-tert-butyl dicarbonate may be processed as described in Example 1H to provide the title compound.

EXAMPLE 2F tert-butyl 5-[4-fluoro-3-(trimethylstannyl)phenyl]-4,6-dioxo-3,4,5,6,7,9-hexahydro-1H,10H-dipyrano[3,4-b:4,3-e]pyridine-10-carboxylate The product from Example 2E, hexamethylditin and tetrakis(triphenylphosphine)palladium(0) may be processed as described in Example 1I to provide the title compound.

EXAMPLE 2G 5-(4-fluoro-3-[I¹²⁵]iodophenyl)-5,10-dihydro-1H,3H-dipyrano[3,4-b:4,3-e]pyridine-4,6(7H,9H)-dione The product from Example 2F and sodium [I¹²⁵]iodide may be processed as described in Example 1K to provide the title compound.

EXAMPLE 3

5-(3-[I125]iodo-4-methylphenyl)-5,10-dihydro-1H,3H-dipyrano[3,4-b:4,3-e]pyridine-4,6(7H,9H)-dione

EXAMPLE 3A 3-iodo-4-methylbenzaldehyde

3-Iodo-4-methylbenzoic acid (1.0 g, 3.96 mmol) in dry CH₂Cl₂:THF 1:1 (200 mL) was treated with oxalyl chloride (1 mL, 11.9 mmol) and several drops of N,N-dimethylformamide. The mixture was heated at 65° C. for 30 minutes, allowed to cool to ambient temperature, and concentrated under reduced pressure to provide a light yellow solid. The obtained solid was dissolved in THF (200 mL) and treated with a 1M solution of lithium tri-tert-butoxyaluminohydride in THF (4.1 mL, 4.1 mmol) via syringe at −78° C. After 30 minutes at −78° C., a saturated solution of Rochelle's salt was added and the mixture was allowed to warm to ambient temperature. The organic layer was washed in succession with 1N HCl, saturated NaHCO₃ and brine, dried over Na₂SO₄, and concentrated. The resulting residue was purified by flash chromatography using hexanes:ethyl acetate (4:1) as the eluent to provide the title compound as a white solid (300 mg, 18%).

EXAMPLE 3B 5-(3-iodo-4-methylphenyl)-5,10-dihydro-1H,3H-dipyrano[3,4-b:4,3-e]pyridine-4,6(7H,9H)-dione The product from Example 1D (0.097 g, 0.86 mmol), the product from Example 1C (0.49 g) and the product from Example 3A (0.21 g, 0.86 mmol) were processed as described in Example 2D to provide the title compound (0.050 g).

¹H NMR (DMSO-d₆) δ2.27 (s, 3H), 4.04 (s, 4H), 4.51 (m, 4H), 4.87 (s, 1H), 7.09 (m, 1H), 7.21 (d, 1H, J=8.01 Hz), 7.60 (d, 1H, J=1.84 Hz);

MS (ESI−) m/z 436 (M−H)⁻;

Anal. Calcd for C₁₈H₁₆INO₄: C, 49.45; H, 3.69; N, 3.20. Found: C, 49.31; H, 3.92; N, 2.89

EXAMPLE 3C tert-butyl 5-(3-iodo-4-methylphenyl)-4,6-dioxo-3,4,5,6,7,9-hexabydro-1H,10H-dipyrano[3,4-b:4,3-e]pyridine-10-carboxylate The product from Example 3B and di-tert-butyl dicarbonate may be processed as described in Example 1H to provide the title compound.

EXAMPLE 3D tert-butyl 5-(4-methyl-3-(trimethylstannyl)phenyl)-4,6-dioxo-3,4,5,6,7,9-hexahydro-1H,10H-dipyrano[3,4-b:4,3-e]pyridine-10-carboxylate The product from Example 3C, hexamethylditin and tetrakis(triphenylphosphine)palladium(0) may be processed as described in Example 1I to provide the title compound.

EXAMPLE 3E 5-(3-[$I^{125}$]iodo-4-methylphenyl)-5,10-dihydro-1H,3H-dipyrano[3,4-b:4,3-e]pyridine-4,6(7H,9H)-dione The product from Example 3D and sodium [$I^{125}$]iodide may be processed as described in Example 1K to provide the title compound.

EXAMPLE 4

5-[3-[$I^{125}$]iodo-4-(trifluoromethyl)phenyl]-5,10-dihydro-1H,3H-dipyrano[3,4-b:4,3-e]pyridine-4,6(7H,9H)-dione

EXAMPLE 4A

[3-nitro-4-(trifluoromethyl)phenyl]methanol 4-(Trifluoromethyl)benzoic acid (15 g, 78.9 mmol) in 90 mL of concentrated sulfuric acid was treated dropwise with a mixture of fuming nitric acid (2 mL) and sulfuric acid (24 mL). The reaction mixture was stirred at ambient temperature for 48 hours and quenched into ice-water. The resulting precipitate (12 g) was collected by filtration, washed with water and dried under reduced pressure. The resulting dry solid (12 g) was dissolved in THF (300 mL), cooled to 0° C., treated with 1M borane-tetrahydrofuran complex (80 mL) and stirred at ambient temperature overnight. Methanol (5 mL) was added dropwise followed by dropwise addition of concentrated HCl (5 mL), refluxed for 1 hour and evaporated to dryness and partitioned between water and diethyl ether. The organic layer was dried over MgSO$_4$ and concentrated under reduced pressure. The residue was chromatographed on silica gel eluting with 30% ethyl acetate hexanes to provide the title compound (3.6 g, 20% yield).

$^1$HNMR (CDCl$_3$) δ4.9 (s, 2H), 7.7 (d, 1H), 7.8 (d, 1H), 7.9 (s, 1H).

EXAMPLE 4B

[3-amino-4-(trifluoromethyl)phenyl]methanol

The product from Example 4A (3.6 g, 16.28 mmol) in methanol (100 mL) was hydrogenated in the presence of a catalytic amount of Pd /C for 4 hours. The catalyst was filtered off and the volatiles were evaporated to yield 2.7 g of the title compound.

$^1$H NMR (CDCl$_3$) δ4.62 (s, 2H), 6.75 (m, 2H), 7.5 (d, 1H).

EXAMPLE 4C

[3-iodo-4-(trifluoromethyl)phenyl]methanol

The product from Example 4B (0.76 g, 4 mmol) in water (8 mL) at 0° C. was treated with concentrated H$_2$SO$_4$ (3 mL) and then treated dropwise with an aqueous solution of sodium nitrite (0.41 g, 6 mmol) keeping the temperature below 10° C. After stirring for 1 hour, this solution was then added dropwise to a solution of KI (0.83 g, 5 mmol) in water (10 mL). The resulting mixture was heated to 60° C. for 2 hours, cooled to ambient temperature and extracted with ethyl acetate. The organic layer was washed in succession with 10% sodium bicarbonate, 1M sodium thiosulfate, 10% hydrochloric acid, aqueous sodium bicarbonate, dried over MgSO$_4$ and concentrated to provide the title compound.

$^1$H NMR (CDCl$_3$) δ4.7 (s, 2H), 7.4 (d, 1H), 7.63 (d, 1H), 8.01 (s, 1H).

EXAMPLE 4D 3-iodo-4-(trifluoromethyl)benzaldehyde

The product from Example 4C in chloroform (60 mL) was treated with manganese dioxide (1.45 g, 16 mmol). After refluxing for 12 hours, the mixture was allowed to cool to ambient temperature, filtered and the filtrate concentrated under reduced pressure. The residue was chromatographed on silica gel eluting with 15% ethyl acetate:hexanes to provide the title compound (0.5 g, 42% yield).

$^1$H NMR (CDCl$_3$) δ7.81 (d, 1H), 7.95 (d, 1H), 8.5 (s, 1H), 10.01 (s, 1H).

EXAMPLE 4E

5-[3-iodo-4-(trifluoromethyl)phenyl]-5,10-dihydro-1H,3H-dipyrano[3,4-b:4,3-e]pyridine-4,6(7H,9H)-dione The product from Example 1D (0.09 g, 0.8 mmol), the product from Example 4D (0.24 g, 0.8 mmol) and the product from Example 1C (0.09 g, 0.8 mmol) in ethanol (2 mL) were stirred in a sealed tube at 80° C. for 48 hours. The reaction mixture was concentrated and the residue was chromatographed on silica gel eluting with 5% ethanol/methylene chloride to provide the title compound as the off-white solid (0.25 g).

$^1$H NMR (DMSO-d$_6$) δ4.06 (S, 4H), 4.51 (q, 4H), 4.96 (s, 1H), 7.39 (d, 1H), 7.68 (d, 1H), 7.68 (d, 1H), 7.9 (s, 1H), 10.15 (s, 1H);

MS (ESI–) m/z 490 (M–H)$^-$;

Anal. Calcd for C$_{18}$H$_{13}$NF$_3$IO$_4$: C, 44.01; H, 2.67; N, 2.85. Found: C, 43.64; H, 2.99; N, 2.66

EXAMPLE 4F tert-butyl 5-[3-iodo-4-(trifluoromethyl)phenyl]-4,6-dioxo-3,4,5,6,7,9-hexahydro-1H,10H-dipyrano[3,4-b:4,3-e]pyridine-10-carboxylate The product from Example 4E and di-tert-butyl dicarbonate may be processed as described in Example 1H to provide the title compound.

EXAMPLE 4G tert-butyl 4,6-dioxo-5-[4-(trifluoromethyl)-3-(trimethylstannyl)phenyl]-3,4,5,6,7,9-hexahydro-1H,10H-dipyrano[3,4-b:4,3-e]pyridine-10-carboxylate The product from Example 4F, hexamethylditin and tetrakis(triphenylphosphine)palladium(0) may be processed as described in Example 1I to provide the title compound.

EXAMPLE 4H

5-[3-[$I^{125}$]iodo-4-(trifluoromethyl)phenyl]-5,10-dihydro-1H,3H-dipyrano[3,4-b:4,3-e]pyridine-4,6(7H,9H)-dione The product from Example 4G and sodium [$I^{125}$]iodide may be processed as described in Example 1K to provide the title compound.

EXAMPLE 5

9-(3-[$I^{125}$]iodo-4-methylphenyl)-5,9-dihydro-3H-furo[3,4-b]pyrano[4,3-e]pyridine-1,8(4H,7H)-dione

EXAMPLE 5A methyl 4-(3-iodo-4-methylphenyl)-2-methyl-5-oxo-4,5,6,8-tetrahydro-1H-pyrano[3,4-b]pyridine-3-carboxylate The product from Example 1C (0.34 g, 3.0 mmol), the product from Example 3A (0.74 g, 3.0 mmol) and methyl 3-aminocrotonate (0.35 g, 3.0 mmol) in methanol (8 mL) were heated to 80° C. in a sealed tube for 60 hours. After cooling to ambient temperature, the mixture was filtered and the filter cake washed with methanol and dried to provide the title compound (0.60 g).

EXAMPLE 5B 9-(3-iodo-4-methylphenyl)-5,9-dihydro-3H-furo[3,4-b]pyrano[4,3-e]pyridine-1,8(4H,7H)-dione The product from Example 5A (0.60 g, 1.4 mmol) in chloroform (10 mL) under a nitrogen atmosphere was treated with pyridine (0.13 mL, 1.6 mmol) and pyridinium tribromide (0.48 g, 1.5 mmol) at −10° C. After stirring at −10° C. for 2 hours, the mixture was allowed to warm to ambient temperature and then was treated with 1M HCl and extracted with chloroform. The chloroform layer was dried ($MgSO_4$), filtered, concentrated, heated to 130° C. under nitrogen for 1 hour and cooled to ambient temperature. Purification of the residue by chromatography on silica gel eluting with 10% methanol in dichloromethane provided the title compound (0.28 g).

$^1$H NMR (DMSO-$d_6$) δ2.29 (s, 3H), 4.04 (s, 2H), 4.52 (q, 2H), 4.67 (s, 1H), 4.93 (q, 2H), 7.13 (d, 1H), 7.22 (d, 1H), 7.62 (s, 1H), 10.42 (s, 1H);

MS (ESI+) m/z 424 (M+H)$^+$.

EXAMPLE 5C tert-butyl 9-(3-iodo-4-methylphenyl)-1,8-dioxo-1,3,5,7,8,9-hexahydro-4H-furo[3,4-b]pyrano[4,3-e]pyridine-4-carboxylate The product from Example 5B and di-tert-butyl dicarbonate may be processed as described in Example 1H to provide the title compound.

EXAMPLE 5D tert-butyl 9-[4-methyl-3-(trimethylstannyl)phenyl]-1,8-dioxo-1,3,5,7,8,9-hexahydro-4H-furo[3,4-b]pyrano[4,3-e]pyridine-4-carboxylate The product from Example 5C, hexamethylditin and tetrakis(triphenylphosphine)palladium(0) may be processed as described in Example 1I to provide the title compound.

EXAMPLE 5E 9-(3-[$I^{125}$]iodo-4-methylphenyl)-5,9-dihydro-3H-furo[3,4-b]pyrano[4,3-e]pyridine-1,8(4H,7H)-dione The product from Example 5D and sodium [$I^{125}$]iodide may be processed as described in Example 1K to provide the title compound.

EXAMPLE 6

9-(3-[$I^{125}$]iodo-4-methylphenyl)-5,9-dihydro-3H-furo[3,4-b]pyrano[4,3-e]pyridine-1,8(4H,7H)-dione

EXAMPLE 6A 9-(3-iodo-4-methylphenyl)-5,9-dihydro-3H-furo[3,4-b]pyrano[4,3-e]pyridine-1,8(4H,7H)-dione The enantiomers of the product from Example 5B were separated on a Chiralpak AS chiral HPLC column eluting with 60:40 hexane:ethanol to provide the title compound as the faster moving enantiomer.

$^1$HNMR (DMSO-$d_6$) δ2.29 (s, 3H), 4.04 (s, 2H), 4.52 (q, 2H), 4.67 (s, 1H), 4.93 (q, 2H), 7.13 (d, 1H), 7.22 (d, 1H), 7.62 (s, 1H), 10.42 (s, 1H);

MS (ESI+) m/z 424 (M+H)$^+$;

Anal. Calcd for $C_{17}H_{14}INO_4$: C, 48.25; H, 3.33; N, 3.31. Found: C, 48.47; H, 3.32; N, 3.28.

EXAMPLE 6B tert-butyl 9-(3-iodo-4-methylphenyl)-1,8-dioxo-1,3,5,7,8,9-hexahydro-4H-furo[3,4-b]pyrano[4,3-e]pyridine-4-carboxylate The product from Example 6A and di-tert-butyl dicarbonate may be processed as described in Example 1H to provide the title compound.

EXAMPLE 6C tert-butyl 9-[4-methyl-3-(trimethylstannyl)phenyl]-1,8-dioxo-1,3,5,7,8,9-hexahydro-4H-furo[3,4-b]pyrano[4,3-e]pyridine-4-carboxylate The product from Example 6B, hexamethylditin and tetrakis(triphenylphosphine)palladium(0) may be processed as described in Example 1I to provide the title compound.

EXAMPLE 6D 9-(3-[$I^{125}$]iodo-4-methylphenyl)-5,9-dihydro-3H-furo[3,4-b]pyrano[4,3-e]pyridine-1,8(4H,7H)-dione The product from Example 6C and sodium [$I^{125}$]iodide may be processed as described in Example 1K to provide the title compound.

EXAMPLE 7

9-(3-[$I^{125}$]iodo-4-methylphenyl)-5,9-dihydro-3H-furo[3,4-b]pyrano[4,3-e]pyridine-1,8(4H,7H)-dione

EXAMPLE 7A 9-(3-iodo-4-methylphenyl)-5,9-dihydro-3H-furo[3,4-b]pyrano[4,3-e]pyridine-1,8(4H,7H)-dione The enantiomers of the product from Example 5B were separated on a Chiralpak AS chiral HPLC column eluting with 60:40 hexane:ethanol to provide the title compound as the slower moving enantiomer.

$^1$H NMR (DMSO-$d_6$) δ2.29 (s, 3H), 4.04 (s, 2H), 4.52 (q, 2H), 4.67 (s, 1H), 4.93 (q, 2H), 7.13 (d, 1H), 7.22 (d, 1H), 7.62 (s, 1H), 10.42 (s, 1H);

MS (ESI+) m/z 424 (M+H)$^+$;

Anal. Calcd for $C_{17}H_{14}INO_4$: C, 48.25; H, 3.33; N, 3.31. Found: C, 48.60; H, 3.30; N, 3.31.

EXAMPLE 7B tert-butyl 9-(3-iodo-4-methylphenyl)-1,8-dioxo-1,3,5,7,8,9-hexahydro-4H-furo[3,4-b]pyrano[4,3-e]pyridine-4-carboxylate The product from Example 7A and di-tert-butyl dicarbonate may be processed as described in Example 1H to provide the title compound.

EXAMPLE 7C tert-butyl 9-[4-methyl-3-(trimethylstannyl)phenyl]-1,8-dioxo-1,3,5,7,8,9-hexahydro-4H-furo[3,4-b]pyrano[4,3-e]pyridine-4-carboxylate The product from Example 7B, hexamethylditin and tetrakis(triphenylphosphine)palladium(0) may be processed as described in Example 1I to provide the title compound.

EXAMPLE 7D 9-(3-[I$^{125}$]iodo-4-methylphenyl)-5,9-dihydro-3H-furo[3,4-b]pyrano[4,3-e]pyridine-1,8(4H,7H)-dione The product from Example 7C and sodium [I$^{125}$]iodide may be processed as described in Example 1K to provide the title compound.

EXAMPLE 8

9-(4-fluoro-3-[I$^{125}$]iodophenyl)-5,9-dihydro-3H-furo[3,4-b]pyrano[4,3-e]pyridine-1,8(4H,7H)-dione

EXAMPLE 8A methyl 4-(4-fluoro-3-iodophenyl)-2-methyl-5-oxo-4,5,6,8-tetrahydro-1H-pyrano[3,4-b]pyridine-3-carboxylate The product from Example 1C (0.34 g, 3.0 mmol), the product from Example 2C (0.74 g, 3.0 mmol) and methyl 3-aminocrotonate (0.35 g, 3.0 mmol) in methanol (8 mL) were processed as described in Example 5A to provide the title compound (0.60 g).

EXAMPLE 8B 9-(4-fluoro-3-iodophenyl)-5,9-dihydro-3H-furo[3,4-b]pyrano[4,3-e]pyridine-1,8(4H,7H)-dione The product from Example 8A (0.59 g, 1.3 mmol) was processed as described in Example 5B to provide the title compound (0.27 g).

$^1$H NMR (DMSO-d$_6$) δ4.05 (s, 2H), 4.52 (q, 2H), 4.72 (s, 1H), 4.95 (q, 2H), 7.17 (t, 1H), 7.25 (m, 1H), 7.62 (d, 1H), 10.46 (s, 1H);
MS (ESI−) m/z 426 (M−H)$^−$.

EXAMPLE 8C tert-butyl 9-(4-fluoro-3-iodophenyl)-1,8-dioxo-1,3,5,7,8,9-hexahydro-4H-furo[3,4-b]pyrano[4,3-e]pyridine-4-carboxylate The product from Example 8B and di-tert-butyl dicarbonate may be processed as described in Example 1H to provide the title compound.

EXAMPLE 8D tert-butyl 9-[4-fluoro-3-(trimethylstannyl)phenyl]-1,8-dioxo-1,3,5,7,8,9-hexahydro-4H-furo[3,4-b]pyrano[4,3-e]pyridine-4-carboxylate The product from Example 8C, hexamethylditin and tetrakis(triphenylphosphine)palladium(0) may be processed as described in Example 1I to provide the title compound.

EXAMPLE 8E 9-(3-[I$^{125}$]iodo-4-methylphenyl)-5,9-dihydro-3H-furo[3,4-b]pyrano[4,3-e]pyridine-1,8(4H,7H)-dione The product from Example 8D and sodium [I$^{125}$]iodide may be processed as described in Example 1K to provide the title compound.

EXAMPLE 9

(9S)-9-(4-fluoro-3-[I$^{125}$]iodophenyl)-5,9-dihydro-3H-furo[3,4-b]pyrano[4,3-e]pyridine-1,8(4H,7H)-dione

EXAMPLE 9A (9S)-9-(4-fluoro-3-iodophenyl)-5,9-dihydro-3H-furo[3,4-b]pyrano[4,3-e]pyridine-1,8(4H,7H)-dione The enantiomers of the product from Example 8B were separated on a (R, R) Whelk-O chiral HPLC column eluting with 15:2:1 hexane:methanol:dichloromethane to provide the title compound as the faster moving enantiomer which was determined to have an absolute configuration of (S) via X-ray analysis.

X-ray data: MW=427.17, C$_{16}$H$_{11}$NO$_4$FI, crystal dimensions 0.80×0.20×0.20 mm, orthorhombic, P2$_1$2$_1$2$_1$ (#19), a=7.8950(1) Å, b=13.6229(2) Å, c=14.0899(2) Å, V=1515.41(3) Å$^3$, Z=4, D$_{calc}$=1.872 g/cm$^3$, Crystallographic data were collected using Mo Kα radiation (λ=0.71069 Å$^3$). Refinement of the structure using full matrix least squares refinement of 208 parameters on 2907 reflections with I>3.00σ(I) gave R=0.059, R$_w$=0.080.

$^1$H NMR (DMSO-d$_6$) δ4.05 (s, 2H), 4.52 (q, 2H), 4.72 (s, 1H), 4.95 (q, 2H), 7.17 (t, 1H), 7.25 (m, 1H), 7.62 (d, 1H), 10.46 (s, 1H);
MS (ESI−) m/z 426 (M−H)$^−$;
Anal. Calcd for C$_{16}$H$_{11}$FINO$_4$: C, 44.99; H, 2.60; N, 3.28. Found: C, 45.02; H, 2.63; N, 3.24.

EXAMPLE 9B tert-butyl (9S)-9-(4-fluoro-3-iodophenyl)-1,8-dioxo-1,3,5,7,8,9-hexahydro-4H-furo[3,4-b]pyrano[4,3-e]pyridine-4-carboxylate The product from Example 9A and di-tert-butyl dicarbonate may be processed as described in Example 1H to provide the title compound.

EXAMPLE 9C tert-butyl (9S)-9-[3-(1,1-distannyldistannanyl)-4-fluorophenyl]-1,8-dioxo-1,3,5,7,8,9-hexahydro-4H-furo[3,4-b]pyrano[4,3-e]pyridine-4-carboxylate The product from Example 9B, hexamethylditin and tetrakis(triphenylphosphine)palladium(0) may be processed as described in Example 1I to provide the title compound.

EXAMPLE 9D (9S)-9-(4-fluoro-3-[I$^{125}$]iodophenyl)-5,9-dihydro-3H-furo[3,4-b]pyrano[4,3-e]pyridine-1,8(4H,7H)-dione The product from Example 9C and sodium [I$^{125}$]iodide may be processed as described in Example 1K to provide the title compound.

EXAMPLE 10

(9R)-9-(4-fluoro-3-[I$^{125}$]iodophenyl)-5,9-dihydro-3H-furo[3,4-b]pyrano[4,3-e]pyridine-1,8(4H,7H)-dione

EXAMPLE 10A (9R)-9-(4-fluoro-3-iodophenyl)-5,9-dihydro-3H-furo[3,4-b]pyrano[4,3-e]pyridine-1,8(4H,7H)-dione The enantiomers of the product from Example 8B were separated on a (R, R) Whelk-O chiral HPLC column eluting with 15:2:1 hexane:methnaol:dichloromethane to provide the title compound as the slower moving enantiomer.

$^1$H NMR (DMSO-d$_6$) δ4.05 (s, 2H), 4.52 (q, 2H), 4.72 (s, 1H), 4.95 (q, 2H), 7.17 (t, 1H), 7.25 (m, 1H), 7.62 (d, 1H), 10.46 (s, 1H);
MS (ESI−) m/z 426 (M−H)$^−$;
Anal. Calcd for C$_{16}$H$_{11}$FINO$_4$: C, 44.99; H, 2.60; N, 3.28. Found: C, 44.95; H, 2.72; N, 2.98.

EXAMPLE 10B tert-butyl (9R)-9-(4-fluoro-3-iodophenyl)-1,8-dioxo-1,3,5,7,8,9-hexahydro-4H-furo[3,4-b]pyrano[4,3-e]pyridine-4-carboxylate The product from Example 10A and di-tert-butyl dicarbonate may be processed as described in Example 1H to provide the title compound.

EXAMPLE 10C tert-butyl (9R)-9-[3-(1,1-distannyldistannanyl)-4-fluorophenyl]-1,8-dioxo-1,3,5,7,8,9-hexahydro-4H-furo[3,4-b]pyrano[4,3-e]pyridine-4-carboxylate The product from Example 10B, hexamethylditin and tetrakis(triphenylphosphine)palladium(0) may be processed as described in Example 1I to provide the title compound.

EXAMPLE 10D (9R)-9-(4-fluoro-3-[$I^{125}$]iodophenyl)-5,9-dihydro-3H-furo[3,4-b]pyrano[4,3-e]pyridine-1,8(4H,7H)-dione The product from Example 10C and sodium [$I^{125}$]iodide may be processed as described in Example 1K to provide the title compound.

EXAMPLE 11

(trans) 9-(4-fluoro-3-[$I^{125}$]iodophenyl)-3-methyl-5,9-dihydro-3H-furo[3,4-b]pyrano[4,3-e]pyridine-1,8(4H,7H)-dione

EXAMPLE 11A methyl 3-amino-2-pentenoate

Methyl 3-oxopentanoate (10 g, 77 mmol) was treated with 2M ammonia in ethanol (200 mL), heated at 80° C. in a sealed tube for 16 hours and concentrated to dryness to provide the title compound.

EXAMPLE 11B methyl 2-ethyl-4-(4-fluoro-3-iodophenyl)-5-oxo-4,5,6,8-tetrahydro-1H-pyrano[3,4-b]pyridin-3-carboxylate The product from Example 11A (1.4 g, 11 mmol), the product from Example 2C (2.9 g, 11 mmol) and the product from Example 1C (1.0 g, 8.8 mmol) were taken up in ethanol (15 mL), heated at 80° C. for 24 hours, stirred at ambient temperature for 36 hours and concentrated. The residue was purified by chromatography on silica gel eluting with 2% methanol in dichloromethane to provide the title compound.
MS (ESI+) m/z 452 (M+H)$^+$;
MS (ESI−) m/z 450 (M−H)$^−$.

EXAMPLE 11C (trans) 9-(4-fluoro-3-iodophenyl)-3-methyl-5,9-dihydro-3H-furo[3,4-b]pyrano[4,3-e]pyridine-1,8(4H,7H)-dione The product from Example 11B (2.8 g, 6.1 mmol) in chloroform (50 mL) was treated with N-bromosuccinimide (1.2 g, 6.7 mmol), stirred at ambient temperature for 20 minutes, concentrated to dryness, heated at 130° C. under nitrogen for 15 minutes and allowed to cool to ambient temperature. The residue was purified on silica gel eluting with ethyl acetate:formic acid:water:hexane (38:1:1:40, then 38:1:1:20 then 38:1:1:10) to provide the title compound as the less polar diastereomer.
$^1$H NMR (DMSO-d$_6$) δ1.42 (d, 3H), 4.05 (s, 2H), 4.55 (AB q, 2H), 4.71 (s, 1H), 5.26 (q, 1H), 7.16 (t, 1H), 7.26 (ddd, 1H), 7.63 (dd, 1H), 10.42 (bs, 1H);
MS (ESI+) m/z 452 (M+H)$^+$;
MS (ESI−) m/z 450 (M−H)$^−$;
Anal. Calcd for C$_{17}$H$_{13}$NO$_4$FI: C, 46.28; H, 2.97; N, 3.17. Found: C, 46.03; H, 3.05; N, 3.06.

EXAMPLE 11D tert-butyl (trans) 9-(4-fluoro-3-iodophenyl)-3-methyl-1,8-dioxo-1,3,5,7,8,9-hexahydro-4H-furo[3,4-b]pyrano[4,3-e]pyridine-4-carboxylate The product from Example 11C and di-tert-butyl dicarbonate may be processed as described in Example 1H to provide the title compound.

EXAMPLE 11E tert-butyl (trans) 9-[4-fluoro-3-(trimethylstannyl)phenyl]-3-methyl-1,8-dioxo-1,3,5,7,8,9-hexahydro-4H-furo[3,4-b]pyrano[4,3-e]pyridine-4-carboxylate The product from Example 11D, hexamethylditin and tetrakis(triphenylphosphine)palladium(0) may be processed as described in Example 1I to provide the title compound.

EXAMPLE 11F (trans) 9-(4-fluoro-3-[$I^{125}$]iodophenyl)-3-methyl-5,9-dihydro-3H-furo[3,4-b]pyrano[4,3-e]pyridine-1,8(4H,7H)-dione The product from Example 11E and sodium [$I^{125}$]iodide may be processed as described in Example 1K to provide the title compound.

EXAMPLE 12

(cis) 9-(4-fluoro-3-[$I^{125}$]iodophenyl)-3-methyl-5,9-dihydro-3H-furo[3,4-b]pyrano[4,3-e]pyridine-1,8(4H,7H)-dione

EXAMPLE 12A (cis) 9-(4-fluoro-3-iodophenyl)-3-methyl-5,9-dihydro-3H-furo[3,4-b]pyrano[4,3-e]pyridine-1,8(4H,7H)-dione The more polar diastereomer of Example 11C was separated by column chromatography eluting with ethyl acetate:formic acid:water:hexane (38:1:1:40, then 38:1:1:20 then 38:1:1:10) to provide the title compound.
mp 236–238 C;
$^1$H NMR (DMSO-d$_6$) δ1.45 (d, 3H), 4.05 (s, 2H), 4.54 (AB q, 2H), 4.72 (s, 1H), 5.11–5.19 (m, 1H), 7.17 (t, 1H), 7.18–7.24 (m, 1H), 7.62 (dd, 1H), 10.45 (bs, 1H);
MS (ESI+) m/z 442 (M+H)$^+$, 459 (M+NH$_4$)$^+$;
MS (ESI−) m/z 440 (M−H)$^−$;
Anal. Calcd for C$_{17}$H$_{13}$NO$_4$FI 0.5 C$_4$H$_8$O$_2$: C, 47.03; H, 3.53; N, 2.89. Found: C, 46.93; H, 3.42; N, 2.68.

EXAMPLE 12B tert-butyl (cis) 9-(4-fluoro-3-iodophenyl)-3-methyl-1,8-dioxo-1,3,5,7,8,9-hexahydro-4H-furo[3,4-b]pyrano[4,3-e]pyridine-4-carboxylate The product from Example 12A and di-tert-butyl dicarbonate may be processed as described in Example 1H to provide the title compound.

EXAMPLE 12C tert-butyl (cis) 9-[4-fluoro-3-(trimethylstannyl) phenyl]-3-methyl-1,8-dioxo-1,3,5,7,8,9-hexahydro-4H-furo[3,4-b]pyrano[4,3-e]pyridine-4-carboxylate The product from Example 12B, hexamethylditin and tetrakis(triphenylphosphine)palladium(0) may be processed as described in Example 1I to provide the title compound.

EXAMPLE 12D (cis) 9-(4-fluoro-3-[$I^{125}$]iodophenyl)-3-methyl-5,9-dihydro-3H-furo[3,4-b]pyrano[4,3-e]pyridine-1,8 (4H,7H)-dione The product from Example 12C and sodium [$I^{125}$]iodide may be processed as described in Example 1K to provide the title compound.

EXAMPLE 13

(3S,9R)-9-(4-fluoro-3-[$I^{125}$]iodophenyl)-3-methyl-5, 9-dihydro-3H-furo[3,4-b]pyrano[4,3-e]pyridine-1,8 (4H,7H)-dione

EXAMPLE 13A (3S,9R)-9-(4-fluoro-3-iodophenyl)-3-methyl-5,9-dihydro-3H-furo[3,4-b]pyrano[4,3-e]pyridine-1,8 (4H,7H)-dione The cis enantiomers of Example 12A were separated on a Chiralpak AS chiral HPLC column eluting with 50:50 hexane:ethanol to provide the title compound as the faster moving enantiomer. Absolute stereochemistry was determined relative to the X-ray data described in Example 14.

mp 256–258 C;

$^1$H NMR (DMSO-d$_6$) δ1.45 (d, 3H), 4.05 (s, 2H), 4.54 (AB q, 2H), 4.72 (s, 1H), 5.11–5.19 (m, 1H), 7.17 (t, 1H), 7.18–7.24 (m, 1H), 7.62 (dd, 1H), 10.45 (bs, 1H);

MS (ESI+) m/z 442 (M+H)$^+$, 459 (M+NH$_4$)$^+$;

MS (ESI−) m/z 440 (M−H)$^−$;

Anal. Calcd for C$_{17}$H$_{13}$NO$_4$FI: C, 46.28; H, 2.97; N, 3.17. Found: C, 46.35; H, 3.00; N, 3.02.

EXAMPLE 13B tert-butyl (3S,9R)-9-(4-fluoro-3-iodophenyl)-3-methyl-1,8-dioxo-1,3,5,7,8,9-hexahydro-4H-furo[3, 4-b]pyrano[4,3-e]pyridine-4-carboxylate The product from Example 13A and di-tert-butyl dicarbonate may be processed as described in Example 1H to provide the title compound.

EXAMPLE 13C tert-butyl (3S,9R)-9-[4-fluoro-3-(trimethylstannyl) phenyl]-3-methyl-1,8-dioxo-1,3,5,7,8,9-hexahydro-4H-furo[3,4-b]pyrano[4,3-e]pyridine-4-carboxylate The product from Example 13B, hexamethylditin and tetrakis(triphenylphosphine)palladium(0) may be processed as described in Example 1I to provide the title compound.

EXAMPLE 13D (3S,9R)-9-(4-fluoro-3-[$I^{125}$]iodophenyl)-3-methyl-5, 9-dihydro-3H-furo[3,4-b]pyrano[4,3-e]pyridine-1,8 (4H,7H)-dione The product from Example 13C and sodium [$I^{125}$]iodide may be processed as described in Example 1K to provide the title compound.

EXAMPLE 14

(3R,9S)-9-(4-fluoro-3-[$I^{125}$]iodophenyl)-3-methyl-5, 9-dihydro-3H-furo[3,4-b]pyrano[4,3-e]pyridine-1,8 (4H,7H)-dione

EXAMPLE 14A (3R,9S)-9-(4-fluoro-3-iodophenyl)-3-methyl-5,9-dihydro-3H-furo[3,4-b]pyrano[4,3-e]pyridine-1,8 (4H,7H)-dione The cis enantiomers of Example 12A were separated on a Chiralpak AS chiral HPLC column eluting with 50:50 hexane:ethanol to provide the title compound as the slower moving enantiomer. Absolute stereochemistry was determined from X-ray analysis.

X-ray data: MW=441.20, C$_{17}$H$_{13}$NO$_4$FI, crystal dimensions 0.60×0.20×0.20 mm, orthorhombic, P2$_1$2$_1$2$_1$ (#19), a=8.7356(4) Å, b=13.9227(6) Å, c=14.3009(6) Å, V=1739.3 (1) Å$^3$, Z=4, D$_{calc}$=1.685 g/cm$^3$, Crystallographic data were collected using Mo Kα radiation (λ=0.71069 Å$^3$). Refinement of the structure using full matrix least squares refinement of 217 parameters on 3025 reflections with I>3.00σ(I) gave R=0.045, R$_W$=0.061.

mp 256[14] 258 C;

$^1$H NMR (DMSO-d$_6$) δ1.45 (d, 3H), 4.05 (s, 2H), 4.54 (AB q, 2H), 4.72 (s, 1H), 5.11–5.19 (m, 1H), 7.17 (t, 1H), 7.18–7.24 (m, 1H), 7.62 (dd, 1H), 10.45 (bs, 1H);

MS (ESI+) m/z 442 (M+H)$^+$, 459 (M+NH$_4$)$^+$;

MS (ESI−) m/z 440 (M−H)$^−$;

Anal. Calcd for C$_{17}$H$_{13}$NO$_4$FI: C, 46.28; H, 2.97; N, 3.17. Found: C, 46.49; H, 3.10; N, 2.95.

EXAMPLE 14B tert-butyl (3R,9S)-9-(4-fluoro-3-iodophenyl)-3-methyl-1,8-dioxo-1,3,5,7,8,9-hexahydro-4H-furo[3, 4-b]pyrano[4,3-e]pyridine-4-carboxylate The product from Example 14A and di-tert-butyl dicarbonate were processed as described in Example 1H to provide the title compound.

EXAMPLE 14C tert-butyl (3R,9S)-9-[4-fluoro-3-(trimethylstannyl) phenyl]-3-methyl-1,8-dioxo-1,3,5,7,8,9-hexahydro-4H-furo[3,4-b]pyrano[4,3-e]pyridine-4-carboxylate The product from Example 14B, hexamethylditin and tetrakis(triphenylphosphine)palladium(0) were processed as described in Example 1I to provide the title compound.

EXAMPLE 14D (3R,9S)-9-(4-fluoro-3-[$I^{125}$]iodopbenyl)-3-methyl-5, 9-dihydro-3H-furo[3,4-b]pyrano[4,3-e]pyridine-1,8 (4H,7H)-dione The product from Example 14C and sodium [$I^{125}$]iodide were processed as described in Example 1K to provide the title compound.

Ligands Binding Assays

Membrane Preparation: Guinea-pig cardiac ventricles and bladder membranes were prepared by standard procedures, Gopalakrishnan, M., Johnson, D. E., Janis, R. A. & Triggle, D. J. (1991) Journal of Pharmacology and Experimental Therapeutics, 257, 1162–71; Russ, U., Metzger, F., Kickenweiz, E., Hambrock, A., Krippeit-Drews, P. & Quast, U. (1997) Br. J. Pharmacol., 122, 1119–1126. Briefly, ventricles and bladders were quickly removed from male guinea-pigs (Charles River) and placed in ice-cold binding buffer. Tissues were cleansed of adherent connective tissue, chopped into small pieces and disrupted using Tekmar polytron in about 15-vol./g tissue weight. Homogenates were centrifuged at 45,000×g and the membrane pellets were resuspended in the assay buffer. Membrane preparations from other tissues, cells, both clonal and transfected with $K_{ATP}$ subunits, may also be used. Clonal cell lines or transfected cell lines can be cultured by standard tissue culture techniques. When cells were confluent, membrane preparations were made by removal of media followed by scraping the monolayer in ice-cold Tris HCl buffer (pH 7.2). The suspension was then centrifuged at 45,000×g for 20 minutes and the pellet was resuspended in the assay buffer for use in radioligand assays.

Binding Assay: A radioligand of formula (I) such as 9-(4-fluoro-3-[$I^{125}$]iodophenyl)-2,3,5,9-tetrahydro-4H-pyrano[3,4-b]thieno[2,3-e]pyridin-8(7H)-one 1,1-dioxide (Example 1) (specific activity, 2000 Ci/mmol) was stored in ethanol. Prior to use, the desired amount of Example 1 was dried under a gentle stream of nitrogen gas and reconstituted in the assay buffer (usually prepared as a 10×stock). Guinea-pig ventricle membranes were incubated in a total 0.25 mL volume of HEPES buffer (composition, NaCl, 139 mM; KCl, 5 mM, $MgCl_2$, 25 mM; $CaCl_2$, 1.25 mM; pH 7.4 at 25° C.) containing an ATP regenerating system (creatine phosphate (40 mM), creatine phosphokinase (100 enzyme units) and varying concentrations of $Na_2ATP$ (0.01–3 mM) with Example 1 and varying concentrations of test compounds at 37° C. for 90 minutes. These conditions have been previously employed by Gopalakrishnan et al., 1991 (see above), hereby incorporated by reference, wherein the levels of ATP were consistently maintained since free ADP is converted back to ATP by creatine phosphate and creatine is regenerated to creatine phosphate by the enzyme creatine phosphokinase.

Saturation binding of Example 1 was performed with varying concentrations of Example 1. For inhibition assays, samples were incubated in a final volume of 0.25 mL of buffer containing 1–2 nM of Example 1 with varying concentrations of the test compounds. Incubations were terminated by rapid vacuum filtration through GF/B filters followed by rinsing twice with ice-cold 50 mM Tris HCl (pH 7.4). Radioactivity bound to the filters was assessed by gamma counting. Specific radioligand binding is defined by the inclusion of 10 μM of unlabeled Example 1 and was obtained by subtracting the nonspecific binding from the total binding to membranes and filters.

Membrane protein concentration was determined by the method of Lowry et al Gopalakrishnan, M., Triggle, D. J., Rutledge, A., Kwon, Y. W., Bauer, J. A. & Fung, H. L. (1991) Am. J. Physiol., 261, H1979–H1987; Janis, R. A., Maurer, S. C., Sarmiento, J. G., Bolger, G. T. & Triggle, D. J. (1982). Eur. J. Pharmacol., 82, 191–4.

The equilibrium dissociation constant ($K_D$) and maximal density of binding sites (Bmax) of Example 1 was determined by non-linear regression of the saturation binding isotherm. The $K_i$ values were calculated from the concentration inhibition curve by the method of Cheng and Prusoff (1973) Biochem.Pharmacol.,22, 3099–3108. Data is presented as means±S.E.M.

Brief Description of the Results:

Characteristics of Example 1 Binding: Example 1 binds in a saturable manner to membrane preparations from the guinea-pig cardiac ventricle. Within the concentration range examined, specific binding was to a single set of saturable binding sites with a $K_D$ value of 5.83±0.77 nM and maximum binding capacity of 107.7±12.7 (n=3) femtomol/mg protein (see FIG. 1A).

Like those previously described for $K_{ATP}$ channel interactions, Example 1 binding was critically dependent on the addition on an ATP-regenerating system in the assay mixture. FIG. 1B shows a displacement profile of unlabeled Example 1. Unlabeled Example 1 displaced specific binding with a Ki value of 5.8 nM in the presence of the ATP regenerating system whereas no specific binding was detected in the presence of just ATP alone.

Pharmacologic Profile of Example 1 Binding: Test compounds displaced binding of Example 1. In addition to unlabeled Example 1, specific binding was displaced by various structurally unrelated compounds that have been described to activate $K_{ATP}$ channels including enantiomers of cromakalim, pinacidil and its analog P1075, Bay X 9228 and its enantiomer Bay X 9228, A-278637 (Abbott Laboratories, Abbott Park, Ill.), and diazoxide. The pseudo-Hill coefficients for competition were close to unity. The rank order potency (Ki) value for displacement of inhibition in cardiac membranes is Example 1 (5.8 nM)>P1075=Bay X 9228>(−)-cromakalim>pinacidil>diazoxide (44.8 uM), Bray, K. M. & Quast, U. (1992) J. Biol. Chem., 267, 11689–92; Hoffman, F. J., Jr., Lenfers, J. B., Niemers, E., Pleiss, U., Scriabine, A. & Janis, R. A. (1993) Biochem. Biophys. Res. Commun., 190, 551–8; and Lowry, O. H., Rosebrough, N. J., Farr, A. L. & Randall, R. J. (1951) J. Biol. Chem, 193, 265–275.

Specific Example 1 binding was also displaced by structurally diverse $K_{ATP}$ channel blockers including the sulfonylurea analogs, glyburide (47.6±9.4 nM) and glipizide (4.5±0.4 μM). Although structurally related to Example 1, binding was unaffected by isradipine (PN 200 110), a 1,4-dihydropyridine calcium channel antagonist.

Comparison of the profile of the novel radioligand with [$^3$H]P1075: Example 1 offers the advantages of an [$^{125}$I]-labeled ligand including its higher specific activity. The typical specific signal is typically 20-fold higher than those observed with [$^3$H]P1075 and, at least in membrane preparations, the specific bound ranges from 75–90% as opposed to [$^3$H]P1075 were specific binding is only about 50% or lower.

|  | [$^3$H]P1075 | [$^{125}$I]A-312110 |
|---|---|---|
| Isotope | tritium | iodine 125 |
| Specific Activity | 120 Ci/mmol | 2000 Ci/mmol |
| Affinity | 9 nM | 5 nM |
| Specific Signal | 300 cpm | 6000 cpm |
| Radioligand Concentration | 5 nM | 0.5–1 nM |
| Ligand Specifically Bound | 50%–60% | 75%–90% |
| Scintillition Liquid | YES | NO |

The compounds of the invention have utility in various pharmaceutical and drug discovery applications:
These include:
(I) High throughput screening of compound libraries,
(II) Screening of cell lines/clones expressing $K_{ATP}$ channel subunits
(III) Identification novel $K_{ATP}$ channel types, (IV) Studies on the mechanism of action of novel A-compounds aimed at the $_{ATP}$-sensitive potassium channel for treatment of urological and neurological indications
(V) Analysis of distribution of these channels in physiological and disease states.

What is claimed is:

1. A compound of formula (I)

wherein
n is an integer of 0–1;
m is an integer of 1–2;
provided that when n is 1, then m is 1;
A is selected from the group consisting of C(O) and S(O)$_2$;
D is selected from the group consisting of O, S and CR$_2$R$_3$;
Z is selected from the group consisting of O and S;
R$_1$ is selected from the group consisting of alkyl, cyano, haloalkoxy, haloalkyl, halogen and nitro; and
R$_2$, R$_3$, R$_4$, R$_5$, R$_6$ and R$_7$ are each independently selected from the group consisting of hydrogen and alkyl;
provided that when A is S(O)$_2$; then D is CR$_2$R$_3$; and further provided that when D is S; then n is 1 and A is C(O).

2. A compound according to claim 1 wherein
R$_1$ is selected from the group consisting of alkyl, haloalkyl and halogen; and
R$_4$, R$_5$, R$_6$ and R$_7$ are each hydrogen.

3. A compound according to claim 1 wherein
n is 0;
A is S(O)$_2$; and
D is CR$_2$R$_3$.

4. A compound according to claim 1 wherein
m is 1;
n is 0;
A is S(O)$_2$;
D is CR$_2$R$_3$;
Z is O; and
R$_2$, R$_3$, R$_4$, R$_5$, R$_6$ and R$_7$ are each hydrogen.

5. A compound according to claim 4 that is selected from the group consisting of
9-(4-fluoro-3-[$^{125}$I]iodophenyl)-2,3,5,9-tetrahydro-4H-pyrano[3,4-b]thieno[2,3-e]pyridin-8(7H)-one 1,1-dioxide;
(R) 9-(4-fluoro-3-[$^{125}$I]iodophenyl)-2,3,5,9-tetrahydro-4H-pyrano[3,4-b]thieno[2,3-e]pyridin-8(7H)-one 1,1-dioxide; and
(S) 9-(4-fluoro-3-[$^{125}$I]iodophenyl)-2,3,5,9-tetrahydro-4H-pyrano[3,4-b]thieno[2,3-e]pyridin-8(7H)-one 1,1-dioxide.

6. A compound according to claim 1 wherein
n is 0;
A is C(O); and
D is CR$_2$R$_3$.

7. A compound according to claim 1 wherein
n is 0;
A is C(O); and
D is O.

8. A compound according to claim 1 wherein
m is 1;
n is 0;
A is C(O);
D is O;
Z is O; and
R$_4$, R$_5$, R$_6$ and R$_7$ are each hydrogen.

9. A compound according to claim 8 selected from the group consisting of
9-(3-[$^{125}$I]iodo-4-methylphenyl)-5,9-dihydro-3H-furo[3,4-b]pyrano[4,3-e]pyridine-1,8(4H,7H)-dione;
(+) 9-(3-[$^{125}$I]iodo-4-methylphenyl)-5,9-dihydro-3H-furo[3,4-b]pyrano[4,3-e]pyridine-1,8(4H,7H)-dione;
(−) 9-(3-[$^{125}$I]iodo-4-methylphenyl)-5,9-dihydro-3H-furo[3,4-b]pyrano[4,3-e]pyridine-1,8(4H,7H)-dione;
9-(4-fluoro-3-[$^{125}$I]iodophenyl)-5,9-dihydro-3H-furo[3,4-b]pyrano[4,3-e]pyridine-1,8(4H,7H)-dione;
(9S) 9-(4-fluoro-3-[$^{125}$I]iodophenyl)-5,9-dihydro-3H-furo[3,4-b]pyrano[4,3-e]pyridine-1,8(4H,7H)-dione; and
(9R) 9-(4-fluoro-3-[$^{125}$I]iodophenyl)-5,9-dihydro-3H-furo[3,4-b]pyrano[4,3-e]pyridine-1,8(4H,7H)-dione.

10. A compound according to claim 1 wherein
n is 0;
A is C(O);
D is O;
R$_4$, R$_5$ and R$_6$ are each hydrogen; and
R$_7$ is alkyl.

11. A compound according to claim 1 wherein
m is 1;
n is 0;
A is C(O);
D is O;
Z is O;
R$_4$, R$_5$ and R$_6$ are each hydrogen; and
R$_7$ is alkyl.

12. A compound according to claim 11 selected from the group consisting of
(trans) 9-(4-fluoro-3-[$^{125}$I]iodophenyl)-3-methyl-5,9-dihydro-3H-furo[3,4-b]pyrano[4,3-e]pyridine-1,8(4H,7H)-dione;
(cis) 9-(4-fluoro-3-[$^{125}$I]iodophenyl)-3-methyl-5,9-dihydro-3H-furo[3,4-b]pyrano [4,3-e]pyridine-1,8(4H,7H)-dione; and
(3R,9S)-9-(4-fluoro-3-[$^{125}$I]iodophenyl)-3-methyl-5,9-dihydro-3H-furo[3,4-b]pyrano[4,3-e]pyridine-1,8(4H,7H)-dione.

13. A compound according to claim 11 that is (3S,9R)-9-(4-fluoro-3-[$^{125}$I]iodophenyl)-3-methyl-5,9-dihydro-3H-furo[3,4-b]pyrano[4,3-e]pyridine-1,8(4H,7H)-dione.

14. A compound according to claim 1 wherein
m is 1;
n is 1;

A is C(O); and
D is O.

15. A compound according to claim 1 wherein
m is 1;
n is 1;
A is C(O);
D is O; and
$R_4$, $R_5$, $R_6$ and $R_7$ are each hydrogen.

16. A compound according to claim 1 wherein
m is 1;
n is 1;
A is C(O);
D is O;
Z is O; and
$R_4$, $R_5$, $R_6$ and $R_7$ are each hydrogen.

17. A compound according to claim 16 selected from the group consisting of 5-(4-fluoro-3-[$^{125}$I]iodophenyl)-5,10-dihydro-1H,3H-dipyrano[3,4-b:4,3-e]pyridine-4,6(7H,9H)-dione;

5-(3-[$^{125}$I]iodo-4-methylphenyl)-5,10-dihydro-1H,3H-dipyrano[3,4-b:4,3-e]pyridine-4,6(7H,9H)-dione; and 5-[3-[$^{125}$I]iodo-4-(trifluoromethyl)phenyl]-5,10-dihydro-1H,3H-dipyrano[3,4-b:4,3-e]pyridine-4,6(7H,9H)-dione.

* * * * *